United States Patent
Minagawa et al.

(10) Patent No.: US 7,459,441 B2
(45) Date of Patent: Dec. 2, 2008

(54) REMEDIES FOR DRY EYE AND DISEASES ASSOCIATED WITH DRY EYE

(75) Inventors: Yoko Minagawa, Akashi (JP); Atsuko Fujii, Kako-gun (JP); Yukuo Yoshida, Kobe (JP); Satomi Onoue, Moriya (JP); Kazuhisa Kashimoto, Moriya (JP)

(73) Assignees: Senju Pharmaceutical Co., Ltd., Osaka-Shi (JP); Itoham Foods Inc., Kobe-Shi (JP)

( * ) Notice: Subject to any disclaimer, the term of this patent is extended or adjusted under 35 U.S.C. 154(b) by 0 days.

(21) Appl. No.: 10/494,634

(22) PCT Filed: Nov. 5, 2002

(86) PCT No.: PCT/JP02/11490

§ 371 (c)(1), (2), (4) Date: May 27, 2004

(87) PCT Pub. No.: WO03/039577

PCT Pub. Date: May 15, 2003

(65) Prior Publication Data

US 2004/0259796 A1    Dec. 23, 2004

(30) Foreign Application Priority Data

Nov. 6, 2001    (JP) ............................ 2001-340355

(51) Int. Cl.
*A61K 38/00* (2006.01)
(52) U.S. Cl. ...................................................... 514/13
(58) Field of Classification Search ........................ None
See application file for complete search history.

(56) References Cited

U.S. PATENT DOCUMENTS 4,745,100 A * 5/1988 Gilbard et al. ................. 514/12
5,856,303 A * 1/1999 Kashimoto et al. ............ 514/12

FOREIGN PATENT DOCUMENTS

| EP | 204447 | 12/1986 |
| EP | 796867 | 9/1997 |
| JP | 5-238950 | 9/1993 |
| JP | 2001-151799 | 6/2001 |

OTHER PUBLICATIONS

Zoulikova et al. Synthesis of Fragments of the Vasoactive Intestinal Peptide (VIP) and Analysis of Their Residual Biological Activities. Collect. Czech. Chem. Commun., 1995, vol. 60, pp. 1229-1235.*
http://www.anaspec.com/products/product.asp?id=31024 accessed online Dec. 21, 2007. p. 1 of 1.*

* cited by examiner

*Primary Examiner*—Cecilia Tsang
*Assistant Examiner*—Marcela M Cordero Garcia
(74) *Attorney, Agent, or Firm*—Wenderoth, Lind & Ponack, L.L.P.

(57) ABSTRACT

Remedies for dry eye and diseases associated with dry eye which contain as the active ingredient peptides represented by the general formula (I):

H-His-Ser-Asp-Ala-Val-Phe-Thr-Asp-Asn-Tyr-Thr-Arg-Leu-Arg-$X_1$-Gln-$X_2$-Ala-Val-$X_3$-$X_4$-Tyr-Leu-$X_5$-$X_6$(SEQ ID NOS: 26-36)    (I)

wherein $X_1$, $X_3$ and $X_4$ represent Lys or Arg, respectively; $X_2$ represents Met, Leu or nLeu; $X_5$ represents a chemical bond, Asn, Asn-Ser, Asn-Ser-Ile, Asn-Ser-Ile-Leu(SEQ ID NO: 37) or Asn-Ser-Ile-Leu-Asn-$X_7$(SEQ ID NOS: 38-43) (wherein $X_7$ represents a chemical bond, Gly, etc.); and $X_6$ represents —OH or —$NH_2$, or pharmaceutically acceptable salts thereof:.

2 Claims, 2 Drawing Sheets

REMEDIES FOR DRY EYE AND DISEASES ASSOCIATED WITH DRY EYE

This application is a U.S. national stage of International Application No. PCT/JP02/11490 filed Nov. 5, 2002.

TECHNICAL FIELD

The present invention relates to remedies for dry eye and diseases associated with dry eye.

BACKGROUND ART

Tears play an important role in maintaining the normal visual function. Tears cover the surface of cornea and conjunctiva to retain the wettability thereof and, at the same time, tears fill a depression due to a microvillus on the corneal surface to make the surface smooth, therefore, it becomes possible to obtain a clear image. In addition, epithelial cells of cornea and conjunctiva actively metabolize cellular components and unnecessary cells and metabolites are detached and discharged from the most superficial surface, tears not only wash out them but also supplement necessary oxygen and nutrients. Further, tears wash out foreign matters which intrude on the surface of cornea and conjunctiva, and play a role of defending infection against viruses, bacteria and fungi which have invaded from the outside by the bacteriostatic action of tears. Furthermore, tears work as a synovia between an eyelid and cornea and conjunctiva so that nictitating and eyeball movement are smoothly done. Thus, tears are a minor amount of fluid for forming a slight thin film on the surface of cornea and conjunctiva, and are indispensable for maintaining the transparency and the homeostatis of cornea by various elaborate mechanisms.

The state where a secretion disorder of tears causes abnormality on the surface of cornea and conjunctiva is generally called dry eye. When a disorder of cornea and conjunctiva due to dry eye is caused, supplement of artificial tears, dropping of a viscoelastic substance having high moisture retention such as hyaluronic acid into eyes, and use of dry eye spectacles for keeping the eye surface wet and ameliorating dry symptom are performed. However, while symptom can be ameliorated by these symptomatic treatment methods, these treatment methods are not an etiotropic method for fundamental treatment. Since it is thought that tears have the effect of curing corneal and conjunctival disorder due to dry eye by their natural function as described above, a compound which directly acts on lacrimal gland and promotes tear secretion is expected to be a useful remedy for dry eye and diseases associated with dry eye.

Lacrimal glands are controlled by parasympathetic nerve and sympathetic nerve and the former is dominant. Parasympathetic nerve secretes acetylcholine and VIP (Vasoactive Intestinal Peptide). On the other hand, sympathetic nerve secretes norepinephrine and neuropeptide Y. Acetylcholine, norepinephrine and VIP mainly stimulate lacrimal glands (Dartt D A et al., Adv Eep Med Biol 438: 113-121, 1998). Acetylcholine is shown to activate muscarinic cholinergic route and be involved also in lacrimal secretion (Nakamura M et al., Curr Eye Res 16: 614-619, 1997). Norepinephrine is a sympathomimetic amine which binds to adrenaline α and β receptors, and secretes tear protein via an $α_1$ adrenaline receptor (Dartt D A, Curr Eye Res 8:619-636, 1989). VIP is a peptide having various biological activities which relaxes a smooth muscle of a digestive tract and a blood vessel, and it is reported that receptors for this VIP are present in lacrimal glands (Hodges R R et al., Invest Opthalmol Vis Sci 38:610-619, 1997), and actually promotes secretion of protein from lacrimal glands (Dartt D A et al., Am J Physiol 247:G502-509, 1984).

As described above, distribution of receptors such as muscarine, norepinephrine or VIP in lacrimal glands, and further, participation in lacrimal secretion have been shown. However, currently, these physiologically active ingredients have not been put into practice yet as an agent for preventing or treating dry eye based on the lacrimal secretion promoting activity. With respect to VIP, U.S. Pat. No. 4,745,100 discloses a method of promoting lacrimal secretion by topical administration, but there is no specific description of VIP derivatives therein. In addition, peptides exhibiting excellent bronchodilator activities and the digestive tract movement inhibiting activities as VIP derivatives are disclosed in JP-A 8-333276 and JP-A 2001-151799, respectively, but there are no description regarding lacrimal secretion and dry eye in these publications.

OBJECTS OF THE INVENTION

An object of the present invention is to provide a remedy for dry eye and diseases associated with dry eye by promotion of lacrimal secretion.

SUMMARY OF THE INVENTION

The present inventors studied intensively paying their attention to the lacrimal secretion promoting activity harbored by VIP and, as a result, found that VIP derivatives shown in JP-A 8-333276 and JP-A 2001-151799 have an excellent lacrimal secretion promoting activity. They have further studied, which has resulted in completion of the present invention.

That is, the present invention provides:

(1) A remedy for dry eye or diseases associated with dry eye which comprises a peptide represented by the general formula (I):

H-His-Ser-Asp-Ala-Val-Phe-Thr-Asp-Asn-Tyr-Thr-Arg-Leu-Arg-$X_1$-Gln-$X_2$-Ala-Val-$X_3$-$X_4$-Tyr-Leu-$X_5$-$X_6$(SEQ ID NOS: 26-36)　　　(I)

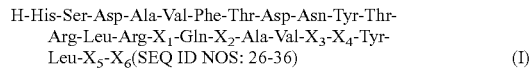

wherein $X_1$, $X_3$ and $X_4$ represent Lys or Arg, respectively; $X_2$ represents Met, Leu or nLeu; $X_5$ represents a chemical bond, Asn, Asn-Ser, Asn-Ser-Ile, Asn-Ser-Ile-Leu(SEQ ID NO: 37) or Asn-Ser-Ile-Leu-Asn-$X_7$(SEQ ID NOS: 38-43) (wherein $X_7$ represents a chemical bond, Gly, Gly-Lys, Gly-Lys-Arg, Gly-Arg or Gly-Arg-Arg); $X_6$ represents —OH or —$NH_2$, provided that, when $X_1$, $X_3$ and $X_4$ are Lys, $X_5$ is Asn-Ser-Ile-Leu-Asn-$X_7$(SEQ ID NOS: 38-43), $X_7$ is a chemical bond, and $X_6$ is —$NH_2$, then $X_2$ represents Leu or nLeu, or a pharmaceutically acceptable salt thereof;

(2) The remedy according to the above (1), wherein $X_5$ is Asn-Ser-Ile-Leu-Asn-$X_7$(SEQ ID NOS: 38-43), and $X_7$ is Gly, Gly-Lys, Gly-Lys-Arg, Gly-Arg or Gly-Arg-Arg in the general formula (I).

(3) The remedy according to the above (1), wherein $X_5$ is a chemical bond, Asn, Asn-Ser, Asn-Ser-Ile, Asn-Ser-Ile-Leu (SEQ ID NO: 37) or Asn-Ser-Ile-Leu-Asn-$X_7$(SEQ ID NOS: 38-43) (wherein $X_7$ is a chemical bond) in the general formula (I);

(4) The remedy according to the above (1), wherein $X_1$, $X_3$ and $X_4$ are Arg, $X_2$ is Leu, $X_5$ is Asn-Ser-Ile-Leu-Asn-$X_7$ (SEQ ID NOS: 38-43), $X_7$ is Gly-Arg-Arg, and $X_6$ is —$NH_2$ in the general formula (I);

(5) The remedy according to the above (1), wherein $X_1$, $X_3$ and $X_4$ are Lys, $X_2$ is Leu, $X_5$ is a chemical bond, and $X_6$ is —$NH_2$ in the general formula (I);

(6) The remedy according to any one of the above (1) to (5), which is a preparation topically administered to the eye;

(7) The remedy according to the above (6), wherein the preparation topically administered to the eye is eye drops;

(8) A pharmaceutical composition for treating dry eye or diseases associated with dry eye, which comprises a peptide represented by the general formula (I):

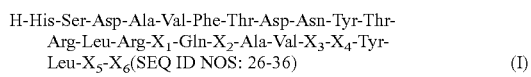

(I)

wherein $X_1$, $X_3$ and $X_4$ represent Lys or Arg, respectively; $X_2$ represents Met, Leu or nLeu; $X_5$ represents a chemical bond, Asn, Asn-Ser, Asn-Ser-Ile, Asn-Ser-Ile-Leu (SEQ ID NO: 37) or Asn-Ser-Ile-Leu-Asn-$X_7$(SEQ ID NOS: 38-43) (wherein $X_7$ represents a chemical bond, Gly, Gly-Lys, Gly-Lys-Arg, Gly-Arg or Gly-Arg-Arg); $X_6$ represents —OH or —$NH_2$, provided that, when $X_1$, $X_3$ and $X_4$ are Lys, $X_5$ is Asn-Ser-Ile-Leu-Asn-$X_7$(SEQ ID NOS: 38-43), $X_7$ is a chemical bond, and $X_6$ is —$NH_2$, then $X_2$ represents Leu or nLeu, or a pharmaceutically acceptable salt thereof and a pharmaceutically acceptable carrier;

(9) The pharmaceutical composition according to the above (8), wherein $X_5$ is Asn-Ser-Ile-Leu-Asn-$X_7$(SEQ ID NOS: 38-43), and $X_7$ is Gly, Gly-Lys, Gly-Lys-Arg, Gly-Arg or Gly-Arg-Arg in the general formula (I);

(10) The pharmaceutical composition according to the above (8), wherein $X_5$ is a chemical bond, Asn, Asn-Ser, Asn-Ser-Ile, Asn-Ser-Ile-Leu(SEQ ID NO: 37) or Asn-Ser-Ile-Leu-Asn-$X_7$(SEQ ID NOS: 38-43) (wherein $X_7$ is a chemical bond) in the general formula (I);

(11) The pharmaceutical composition according to the above (8), wherein $X_1$, $X_3$ and $X_4$ are Arg, $X_2$ is Leu, $X_5$ is Asn-Ser-Ile-Leu-Asn-$X_7$(SEQ ID NOS: 38-43), $X_7$ is Gly-Arg-Arg, and $X_6$ is —$NH_2$ in the general formula (I);

(12) The pharmaceutical composition according to the above (8), wherein $X_1$, $X_3$ and $X_4$ are Lys, $X_2$ is Leu, $X_5$ is a chemical bond, and $X_6$ is —$NH_2$ in the general formula (I);

(13) The pharmaceutical composition according to any one of the above (8) to (12), which is a composition topically administered to the eye;

(14) The pharmaceutical composition according to the above (13), wherein the composition topically administered to the eye is eye drops;

(15) Use of a peptide represented by the general formula (I):

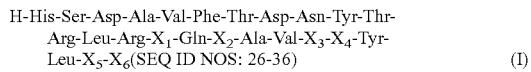

(I)

wherein $X_1$, $X_3$ and $X_4$ each represent Lys or Arg, respectively; $X_2$ represents Met, Leu or nLeu; $X_5$ represents a chemical bond, Asn, Asn-Ser, Asn-Ser-Ile, Asn-Ser-Ile-Leu (SEQ ID NO: 37) or Asn-Ser-Ile-Leu-Asn-$X_7$(SEQ ID NOS: 38-43) (wherein $X_7$ represents a chemical bond, Gly, Gly-Lys, Gly-Lys-Arg, Gly-Arg or Gly-Arg-Arg); $X_6$ represents —OH or —$NH_2$, provided that, when $X_1$, $X_3$ and $X_4$ are Lys, $X_5$ is Asn-Ser-Ile-Leu-Asn-$X_7$(SEQ ID NOS: 38-43), $X_7$ is a chemical bond, and $X_6$ is —$NH_2$, then $X_2$ represents Leu or nLeu, or a pharmaceutically acceptable salt thereof for preparing a medicament for treating dry eye or diseases associated with dry eye;

(16) The use according to the above (15), wherein $X_5$ is Asn-Ser-Ile-Leu-Asn-$X_7$(SEQ ID NOS: 38-43), and $X_7$ is Gly, Gly-Lys, Gly-Lys-Arg, Gly-Arg or Gly-Arg-Arg in the general formula (I);

(17) The use according to the above (15), wherein $X_5$ is a chemical bond, Asn, Asn-Ser, Asn-Ser-Ile, Asn-Ser-Ile-Leu (SEQ ID NO: 37) or Asn-Ser-Ile-Leu-Asn-$X_7$(SEQ ID NOS: 38-43) (wherein $X_7$ is a chemical bond) in the general formula (I);

(18) The use according to the above (15), wherein $X_1$, $X_3$ and $X_4$ are Arg, $X_2$ is Leu, $X_5$ is Asn-Ser-Ile-Leu-Asn-$X_7$ (SEQ ID NOS: 38-43), $X_7$ is Gly-Arg-Arg, and $X_6$ is —$NH_2$ in the general formula (I);

(19) The use according to the above (15), wherein $X_1$, $X_3$ and $X_4$ are Lys, $X_2$ is Leu, $X_5$ is a chemical bond, and $X_6$ is —$NH_2$ in the general formula (I);

(20) The use according to any one of the above (15) to (19), wherein the medicament is a medicament topically administered to the eye;

(21) The use according to the above (20), wherein the medicament topically administered to the eye is eye drops;

(22) A method for treating dry eye or diseases associated with dry eye, which comprises administering an effective amount of a peptide represented by the general formula (I):

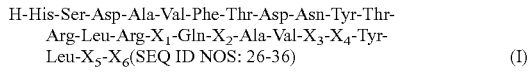

(I)

wherein $X_1$, $X_3$ and $X_4$ represent Lys or Arg, respectively; $X_2$ represents Met, Leu or nLeu; $X_5$ represents a chemical bond, Asn, Asn-Ser, Asn-Ser-Ile, Asn-Ser-Ile-Leu(SEQ ID NO: 37) or Asn-Ser-Ile-Leu-Asn-$X_7$(SEQ ID NOS: 38-43) (wherein $X_7$ represents a chemical bond, Gly, Gly-Lys, Gly-Lys-Arg, Gly-Arg or Gly-Arg-Arg); $X_6$ represents —OH or —$NH_2$, provided that, when $X_1$, $X_3$ and $X_4$ are Lys, $X_5$ is Asn-Ser-Ile-Leu-Asn-$X_7$(SEQ ID NOS: 38-43), $X_7$ is a chemical bond, and $X_6$ is —$NH_2$, then $X_2$ represents Leu or nLeu, or a pharmaceutically acceptable salt thereof to a warm-blooded animal in need of treatment of dry eye or diseases associated with dry eye;

(23) The method according to the above (22), wherein $X_5$ is Asn-Ser-Ile-Leu-Asn-$X_7$(SEQ ID NOS: 38-43), and $X_7$ is Gly, Gly-Lys, Gly-Lys-Arg, Gly-Arg or Gly-Arg-Arg in the general formula (I);

(24) The method according to the above (22), wherein $X_5$ is a chemical bond, Asn, Asn-Ser, Asn-Ser-Ile, Asn-Ser-Ile-Leu (SEQ ID NO: 37) or Asn-Ser-Ile-Leu-Asn-$X_7$(SEQ ID NOS: 38-43) (wherein $X_7$ is a chemical bond) in the general formula (I);

(25) The method according to the above (22), wherein $X_1$, $X_3$ and $X_4$ are Arg, $X_2$ is Leu, $X_5$ is Asn-Ser-Ile-Leu-Asn-$X_7$ (SEQ ID NOS: 38-43), $X_7$ is Gly-Arg-Arg, and $X_6$ is —$NH_2$ in the general formula (I); and

(26) The method according to the above (22), wherein $X_1$, $X_3$ and $X_4$ are Lys, $X_2$ is Leu, $X_5$ is a chemical bond, and $X_6$ is —$NH_2$ in the general formula (I).

DETAILED DESCRIPTION OF THE INVENTION

Figure 1:
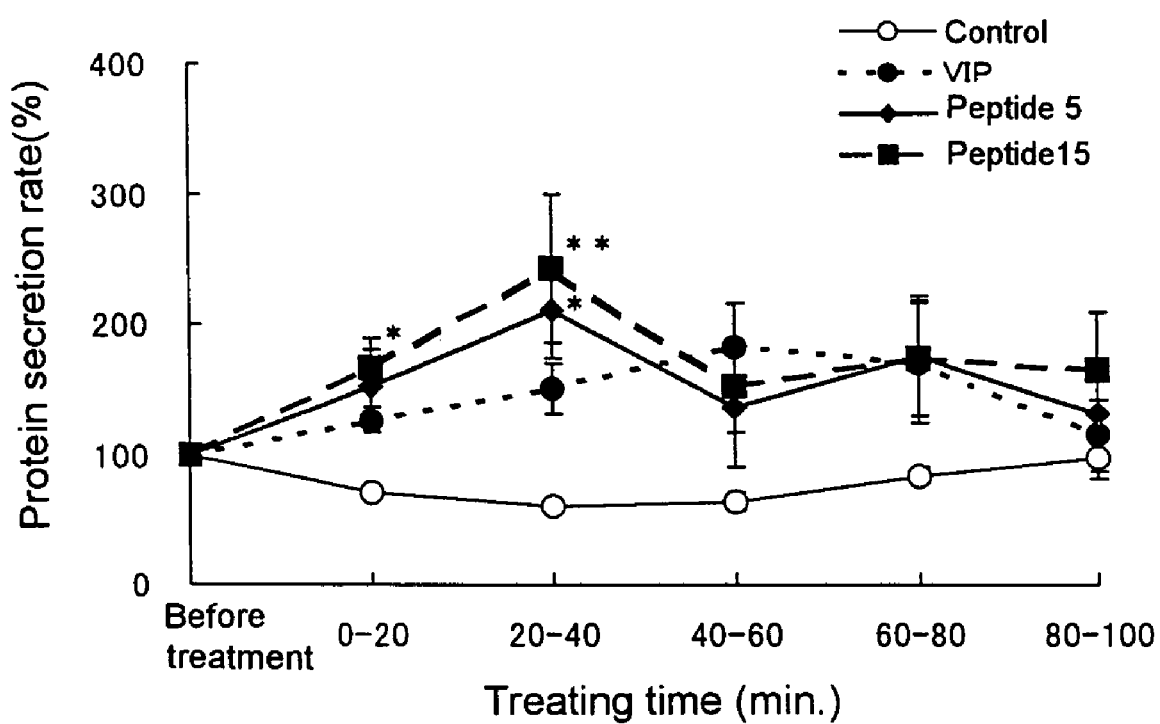
FIG. 1 shows secretion rates of protein from isolated lacrimals gland of rabbits when VIP, Peptide 5 or Peptide 15 is reacted with the lacrimal gland.

The VIP derivative used in treatment of dry eye and diseases associated with dry eye of the present invention is a peptide represented by the general formula (I), and $X_1$, $X_3$ and $X_4$ are Lys or Arg. $X_2$ is Met, Leu or nLeu, preferably Leu. $X_5$ can be a chemical bond, Asn, Asn-Ser, Asn-Ser-Ile, Asn-Ser-Ile-Leu(SEQ ID NO: 37) or Asn-Ser-Ile-Leu-Asn-$X_7$(SEQ ID NOS: 38-43), preferably a chemical bond or Asn-Ser-Ile-Leu-Asn-$X_7$(SEQ ID NOS: 38-43). When $X_5$ is Asn-Ser-Ile-Leu-Asn-$X_7$(SEQ ID NOS: 38-43), $X_7$ is a chemical bond, Gly, Gly-Lys, Gly-Lys-Arg, Gly-Arg or Gly-Arg-Arg, most preferably Gly-Arg-Arg. $X_6$ is —OH or —NH$_2$, more preferably —NH$_2$.

Representative examples of the VIP derivative represented by the general formula (I) of the present invention include peptides 1 to 25 in Table 1 (referred to as Peptides 1 to 25, respectively), and the like. These are peptides corresponding to SEQ ID NOs: 1 to 25 in Sequence Listing hereinafter. Inter alia, Peptide 5 and Peptide 15 are advantageously used.

Peptides 1 to 25 (corresponding to SEQ ID NOs: 1 to 25 shown in Sequence Listing)

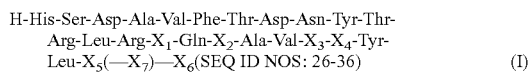

(I)

TABLE 1

| Peptide | $X_1$ | $X_2$ | $X_3$ | $X_4$ | $X_5$ | $X_7$ | $X_6$* |
|---|---|---|---|---|---|---|---|
| 1 | Arg | Leu | Arg | Arg | Asn-Ser-Ile-Leu-Asn | Gly | -NH$_2$ |
| 2 | Arg | Leu | Arg | Arg | Asn-Ser-Ile-Leu-Asn | Gly-Lys | -NH$_2$ |
| 3 | Arg | Leu | Arg | Arg | Asn-Ser-Ile-Leu-Asn | Gly-Arg | -NH$_2$ |
| 4 | Arg | Leu | Arg | Arg | Asn-Ser-Ile-Leu-Asn | Gly-Lys-Arg | -NH$_2$ |
| 5 | Arg | Leu | Arg | Arg | Asn-Ser-Ile-Leu-Asn | Gly-Arg-Arg | -NH$_2$ |
| 6 | Arg | Leu | Arg | Arg | Asn-Ser-Ile-Leu-Asn | Gly-Lys-Arg | -OH |
| 7 | Lys | Met | Lys | Lys | Asn-Ser-Ile-Leu-Asn | | -OH |
| 8 | Lys | Met | Lys | Lys | Asn-Ser-Ile-Leu | | -NH$_2$ |
| 9 | Lys | Met | Lys | Lys | Asn-Ser-Ile | | -NH$_2$ |
| 10 | Lys | Met | Lys | Lys | Asn-Ser | | -NH$_2$ |
| 11 | Lys | Met | Lys | Lys | Asn | | -NH$_2$ |
| 12 | Lys | Met | Lys | Lys | -(chemical bond) | | -NH$_2$ |
| 13 | Lys | Leu | Lys | Lys | Asn-Ser | | -NH$_2$ |
| 14 | Lys | Leu | Lys | Lys | Asn | | -NH$_2$ |
| 15 | Lys | Leu | Lys | Lys | -(chemical bond) | | -NH$_2$ |
| 16 | Arg | Met | Arg | Arg | Asn-Ser-Ile-Leu | | -NH$_2$ |
| 17 | Arg | Met | Arg | Arg | Asn-Ser-Ile | | -NH$_2$ |
| 18 | Arg | Met | Arg | Arg | Asn-Ser | | -NH$_2$ |
| 19 | Arg | Met | Arg | Arg | Asn | | -NH$_2$ |
| 20 | Arg | Met | Arg | Arg | -(chemical bond) | | -NH$_2$ |
| 21 | Arg | Leu | Arg | Arg | Asn-Ser-Ile-Leu | | -NH$_2$ |
| 22 | Arg | Leu | Arg | Arg | Asn-Ser-Ile | | -NH$_2$ |
| 23 | Arg | Leu | Arg | Arg | Asn-Ser | | -NH$_2$ |
| 24 | Arg | Leu | Arg | Arg | Asn | | -NH$_2$ |
| 25 | Arg | Leu | Arg | Arg | -(chemical bond) | | -NH$_2$ |

*$X_6$ indicates a carboxyl terminal of an amino acid sequence in Sequence Listing hereinafter.

Examples of a pharmaceutically acceptable salt of the compound of the general formula (I) include salts with an alkali metal such as sodium, potassium and the like; salts with an alkaline earth metal such as calcium, magnesium and the like; salts with an inorganic base such as an aluminum salt, an ammonium salt and the like; salts with an organic base such as trimethylamine, pyridine, picoline, ethanolamine, diethanolamine, triethanolamine, dicyclohexylamine, N,N-dibenzylethylenediamine and the like; salts with an inorganic acid such as hydrochloric acid, hydrobromic acid, nitric acid, sulfuric acid, phosphoric acid and the like; salts with an organic acid such as formic acid, acetic acid, trifluoroacetic acid, fumaric acid, oxalic acid, tartaric acid, lactic acid, maleic acid, citric acid, succinic acid, malic acid, methanesulfonic acid, benzenesulfonic acid, p-toluenesulfonic acid and the like; and salts with a polymer acid such as tannic acid, carboxymethylcellulose, polylactic acid, polyglycolic acid and the like.

The VIP derivative of the general formula (I) can be synthesized according to a known conventional method for synthesizing a peptide as shown, for example, in JP-A 8-333276, JP-A 9-100237, JP-A 11-100399, JP-A 2001-151799 and JP-A 2001-226284.

The VIP derivative of the general formula (I) has the following properties.

First, the VIP derivative has high stability of a molecule in a living body. Although peptides and proteins are rapidly metabolized by peptidase in a living body, the peptides having increased basicity among the VIP derivatives used in the present invention exhibit resistance to metabolism. That is, since the basicity is increased by substituting one or more of 15th, 20th and 21st lysines among amino acids constituting VIP with arginine, and adding a basic amino acid such as lysine or arginine following a glycine residue on a C-terminal side, the strong affinity with acidic polysaccharides which are present in an extremely large amount in a living body is exhibited. By this nature, resistance to degradation by an endopeptidase such as trypsin is increased in a living body. For example, in a trypsin digestion test using Peptide 5, a higher remaining rate than that of VIP is shown in the presence of chondroitin sulfate (Test Example 1). This tendency is demonstrated more clearly in a peptide digestion test using a bronchoalveolar lavage fluid, and the remaining rate of Peptide 5 after 90 minutes is about 1.8-fold as higher as that of VIP (Test Example 2). Due to the aforementioned excellent stability in a living body, these highly basic VIP derivatives have a long-lasting pharmacological activity. In addition, when topically applied to eyes, they can be used as an eye drop preparation which hardly undergoes enzymatic degradation after application to eyes. For example, it is demonstrated in Test Example 5 that application of Peptide 5 to eyes has a longer-lasting lacrimal secretion promoting activity than that of VIP.

In addition, although $17^{th}$ methionine in amino acid residues constituting VIP is easily oxidized, the VIP derivative in which this place is substituted with leucine or norleucine exhibits resistance to oxidation. Therefore, among the VIP derivatives used in the present invention, a 17-leucine-substituted peptide is hardly oxidized, and can be used as stable eye drops.

In the present invention, the VIP derivative of the general formula (I) or a pharmaceutically acceptable salt thereof (hereinafter, referred to as "VIP derivative" in some cases) is systemically or topically administered as a remedy for dry eye and diseases associated with dry eye (hereinafter, abbreviated as "dry eye remedy" in some cases) Systemically, they are administered parenterally (administered as an injectable preparation such as intravenus injection, subcutaneous injection and intramuscular injection, or as a suppository) and orally. Topically, they are administered to skin or eyes.

Examples of a dosage form of a preparation, which is administered parenterally, include injectable preparations, suppositories, and the like. When formulated into an injectable preparation, for example, a solvent (distilled water for injection), a stabilizer (sodium edetate etc.), an isotonic (sodium chloride, glycerin and sugar alcohol such as mannitol etc.), a pH adjusting agent (hydrochloric acid, citric acid, sodium hydroxide etc.) and a suspending agent (methylcellulose etc.) can be used and, when formulated into a suppository, for example, a suppository base (cacao butter, macrogol etc.), and the like can be appropriately selected and used.

Examples of a preparation which is orally administered include powders, granules, tablets, capsules, syrups, solutions, aerosols and the like. When a preparation is formulated into a powder, granules, a tablet and the like, any pharmaceutical carriers which are suitable for formulating a solid preparation, for example, an excipient (starch, glucose, fructose, white sugar etc.), a lubricant (magnesium stearate etc.), a disintegrating agent (starch, crystalline cellulose etc.), a binder (starch, gum arabic etc.) can be used, and a preparation may be coated with a coating agent (gelatin, white sugar etc.). In addition, when a preparation is formulated into a syrup or a solution, for example, a stabilizer (sodium edetate etc.), a suspending agent (gum arabic, carmerose etc.), a corrigent (simple syrup, glucose etc.) and a flavoring agent can be appropriately selected and used.

Examples of a topical preparation include ointments, creams, lotions, nose drops and topical ocular agents, preferably topical ocular agents. Examples of a topical ocular agent include eye drops, ocular ointments and sustained-release preparations, more preferably eye drops. In these topical preparations, in addition to the VIP derivatives of the present invention, for example, known compounds such as an ointment base (vaseline, lanolin etc.), a solvent (physiological saline, purified water etc.), a stabilizer (sodium edetate, citric acid etc.), a wetting agent (glycerin etc.), an emulsifier (polyvinylpyrrolidone etc.), a suspending agent (hydroxypropylmethylcellulose, hydroxymethylcellulose, methylcellulose etc.), a surfactant (Polysorbate 80, polyoxyethylene hydrogenated castor oil etc.), a preservative (benzalkonium chloride, parabens, chlorobutanol etc.), a buffer (boric acid, borax, sodium acetate, citrate buffer, phosphate buffer etc.), an isotonic (sodium chloride, glycerin, mannitol etc.) and a pH adjusting agent (hydrochloric acid, sodium hydroxide etc.) can be appropriately selected and used.

In addition, as an topical ocular sustained-release preparation, molded gels such as collagen and the like, intraocular implants and sclera plugs obtained by molding a biodegradable polymer such as polylactic acid, or non-biodegradable intraocular implants can be used.

Generally, for the purpose of preventing peptides from adsorbing onto a glass or resin container, an adsorption preventing component can be utilized. The adsorption preventing component utilized herein is a compound which hydrophobically binds to a wall surface of a storage container to prevent adhesion, more specifically, a compound which has a hydrophobic group in a molecule and has the surface active action, and an anion-charged protein. Examples of the former include polyoxyethylene alcohol ether, polyoxyethylene fatty acid ester, polyoxyethylene hydrogenated castor oil, glycerin fatty acid ester, sorbitan fatty acid ester, polyoxyethylene sorbitan fatty acid ester and the like, and examples of the latter anion-charged protein include gelatin, albumin, polygenin and the like. Examples of gelatin, are not limited to, but include gelatin purified according to the Japanese Pharmacopoeia and the like. Gelatins as an adsorption preventing component may be used alone or in combination of two or more thereof. As albumin, there are albumins having no antigenicity to a human, and the concentration of albumin to be incorporated is usually about 0.01 to 50 w/v %, preferably about 0.1 to 2.0 w/v %. As a solvent for dissolving an adsorption preventing component and peptides, any solvents can be used as long as they are physiologically acceptable as a solvent for injection, and preferred examples thereof include water for injection according to the Japanese Pharmacopoeia and physiological saline. Alternatively, the effect of adsorption prevention can be obtained by coating silicone on an internal wall of a container.

By administering the dry eye remedy of the present invention to a warm-blooded animal (mammal such as rat, rabbit, cat, dog, pig, monkey and human, birds such as pigeon and chicken and turkey), lacrimal secretion is promoted. When the dry eye remedy of the present invention is administered to an adult patient, a dose per once is usually 0.00001 to 100 mg, preferably 0.0001 to 0.1 mg in case of an injectable preparation, and is usually 0.1 to 500 mg, preferably 1 to 20 mg in case of oral administration, in terms of the VIP derivative. When the remedy is topically applied to eyes of an adult patient, usually, eye drops containing the VIP derivative at 0.001 to 3.0 w/v %, preferably 0.01 to 0.5 w/v % are applied to eyes at 20 to 50 μl per one application, once to eight times per day.

The dry eye remedy of the present invention can contain an appropriate combination of the VIP derivative and other ingredients for treating dry eye depending on the purpose and the necessity. In addition, as long as it is not contrary to the object of the present invention, the remedy can be used by combining with other pharmacologically active ingredients.

The dry eye remedy of the present invention can be used for treating dry eye such as decreased lacrimation, ocular xerosis, Sjögren's syndrome, keratoconjunctivitis sicca, Stevens-Johnson syndrome, dry eye associated with VDT (Visual Display Terminal) work and the like. Further, the present remedy is also useful as a remedy for diseases associated with dry eye such as corneal and conjuntival epithlial disorder, corneal epithelial erosion, corneal ulcer, limbi palpebrales imflammatory, ocular pemphigus, vernal conjunctivitis, allergic conjunctivitis, and the like.

EXAMPLES

Hereinafter, the present invention will be illustrated in more detail by way of Synthesis Examples, Preparation Examples and Test Examples, but the present invention is not limited to them.

The meanings of abbreviations used in the following Synthesis Examples are as follows:
MBHA: p-methylbenzhydrylamine
MeOH: methanol
Boc: t-buthoxycarbonyl group
TFA: trifluoroacetic acid
TEA: triethylamine
$Cl_2$-Bzl: dichlorobenzyl group
Cl-Z: chlorobenzyloxycarbonyl group
Xan: xanthyl group
Tos: p-toluenesulfonyl group
Bzl: benzyl group
OcHex: O-cyclohexyl group
Bom: benzyloxymethyl group
DCC: dicyclohexylcarbodiimide

Synthesis Example 1

Preparation of Peptide 5

Peptide 5 having an amino acid sequence shown in SEQ ID NO: 5 was prepared according to a conventional method of peptide solid phase synthesis.

A MBHA resin HCl salt (polystyrene-1% divinylbenzene copolymer, 100 to 200 mesh) was added to a manual synthesis reaction tank (made of glass, φ6.0×29.5 cm), which was washed with a 2 to 3-fold volume of the resin of MeOH while stirring and, then, washed with $CH_2Cl_2$ (2 to 3-fold volume of the resin) while stirring, to swell the resin. A neutralization reaction was performed with 10% triethylamine/$CH_2Cl_2$, and DCC and N-hydroxybenzotriazole were added to perform a condensation reaction using Boc-Arg(Tos)-OH corresponding to a C-terminal amino acid in an amount of about 2-fold equivalent that of the resin. After the reaction for about 2 hours (with stirring), the reaction mixture was washed with MeOH and $CH_2Cl_2$ and, after confirmation of disappearance of the α-amino group by Kaiser test, deprotection was performed by treatment with 50% TFA/$CH_2Cl_2$ for 30 minutes. Then, the reaction mixture was neutralized with 10% TEA/$CH_2Cl_2$, washed again with MeOH and $CH_2Cl_2$, and Kaiser test was performed again to confirm the deprotecting reaction. After confirmation, in order to perform coupling of $2^{nd}$ Boc-Arg(Tos)-OH from C-terminal, the similar step was repeated. Thereafter, coupling/deprotection was performed successively in an order of Boc-Gly-OH, Boc-Asn(Xan)-OH, Boc-Leu-OH, Boc-Ile-OH, Boc-Ser(Bzl)-OH, Boc-Asn (Xan)-OH, Boc-Leu-OH, Boc-Tyr($Cl_2$-Bzl)-OH, Boc-Arg (Tos)-OH, Boc-Arg(Tos)-OH, Boc-Val-OH, Boc-Ala-OH, Boc-Leu-OH, Boc-Gln(Xan)-OH, Boc-Arg(Tos)-OH, Boc-Arg (Tos)-OH, Boc-Leu-OH, Boc-Arg (Tos)-OH, Boc-Thr (Bzl)-OH, Boc-Tyr($Cl_2$-Bzl)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, to obtain a protected peptide resin corresponding to Peptide 5; His(Bom)-Ser(Bzl)-Asp(OcHex)-Ala-Val-Phe-Thr(SEQ ID NO: 45) (Bzl)-Asp (OcHex)-Asn-Tyr ($Cl_2$-Bzl)-Thr (Bzl)-Arg (Tos)-Leu-Arg(Tos)-Arg(Tos)-Gln-Leu-Ala-Val-Arg(SEQ ID NO: 46) (Tos)-Arg(Tos)-Tyr($Cl_2$-Bzl)-Leu-Asn-Ser(Bzl)-Ile-Leu-Asn-Gly-Arg (SEQ ID NO: 47) (Tos)-Arg(Tos)-MBHA.

To the resulting protected peptide-MBHA resin was added 100 mL of anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography (stepwise gradient between 10% acetonitrile and 50% acetonitrile), followed by lyophilizing to obtain Peptide 5.

Synthesis Example 2

Preparation of Peptide 15

Peptide 15 having an amino acid sequence shown in SEQ ID NO: 15 was synthesized in the same manner as that of Peptide 5. Namely, coupling/deprotection was performed successively on a MBHA resin in an order of Boc-Leu-OH, Boc-Tyr($Cl_2$-Bzl)-OH, Boc-Lys(Cl-Z)-OH, Boc-Lys(Cl-Z)-OH, Boc-Val-OH, Boc-Ala-OH, Boc-Leu-OH, Boc-Gln (Xan)-OH, Boc-Lys(Cl-Z)-OH, Boc-Arg(Tos)-OH, Boc-Leu-OH, Boc-Arg(Tos)-OH, Boc-Thr(Bzl)-OH, Boc-Tyr ($Cl_2$-Bzl)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His (Bom)-OH, to obtain a protected peptide resin corresponding to Peptide 15; His(Bom)-Ser(Bzl)-Asp(OcHex)-Ala-Val-Phe-Thr (SEQ ID NO: 45) (Bzl)-Asp(OcHex)-Asn-Tyr($Cl_2$-Bzl)-Thr(Bzl)-Arg(Tos)-Leu-Arg(Tos)-Lys(Cl-Z)-Gln-Leu-Ala-Val-Lys(SEQ ID NO: 48) (Cl-Z)-Lys(Cl-Z)-Tyr($Cl_2$-Bzl)-Leu-MBHA.

To the resulting protected peptide-MBHA resin was added 100 mL of anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography (stepwise gradient between 10% acetonitrile and 50% acetonitrile), followed by lyophilizing to obtain Peptide 15.

Synthesis Example 3

Preparation of Peptide 16

Peptide 16 having an amino acid sequence shown in SEQ ID NO: 16 was synthesized in the same manner as that of Peptide 5. Namely, coupling/deprotection was performed on a MBHA resin successively in an order of Boc-Leu-OH, Boc-Ile-OH, Boc-Ser(Bzl)-OH, Boc-Asn(Xan)-OH, Boc-Leu-OH, Boc-Tyr($Cl_2$-Bzl)-OH, Boc-Arg(Tos)-OH, Boc-Arg(Tos)-OH, Boc-Val-OH, Boc-Ala-OH, Boc-Met-OH, Boc-Gln(Xan)-OH, Boc-Arg(Tos)-OH, Boc-Arg(Tos)-OH, Boc-Leu-OH, Boc-Arg(Tos)-OH, Boc-Thr(Bzl)-OH, Boc-Tyr($Cl_2$-Bzl)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His(Bom)-OH, to obtain a protected peptide resin corresponding to Peptide 16; His(Bom)-Ser(Bzl)-Asp (OcHex)-Ala-Val-Phe-Thr(SEQ ID NO: 45) (Bzl)-Asp (OcHex)-Asn-Tyr($Cl_2$-Bzl)-Thr(Bzl)-Arg(Tos)-Leu-Arg (Tos)-Arg(Tos)-Gln-Met-Ala-Val-Arg(SEQ ID NO: 49) (Tos)-Arg(Tos)-Tyr($Cl_2$-Bzl)-Leu-Asn-Ser(Bzl)-Ile-Leu-MBHA.

To the resulting protected peptide-MBHA resin was added 100 mL of anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography (stepwise gradient between 10% acetonitrile and 50% acetonitrile), followed by lyophilizing to obtain Peptide 16.

Synthesis Example 4

Preparation of Peptide 17

Peptide 17 having an amino acid sequence shown in SEQ ID NO: 17 was synthesized in the same manner as that of Peptide 5. Namely, coupling/deprotection was performed on a MBHA resin successively in an order of Boc-Ile-OH, Boc-Ser(Bzl)-OH, Boc-Asn(Xan)-OH, Boc-Leu-OH, Boc-Tyr (Cl$_2$-Bzl)-OH, Boc-Arg(Tos)-OH, Boc-Arg(Tos)-OH, Boc-Val-OH, Boc-Ala-OH, Boc-Met-OH, Boc-Gln(Xan)-OH, Boc-Arg(Tos)-OH, Boc-Arg(Tos)-OH, Boc-Leu-OH, Boc-Arg(Tos)-OH, Boc-Thr(Bzl)-OH, Boc-Tyr(Cl$_2$-Bzl)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp (OcHex)-OH, Boc-Ser(Bzl)-OH, and Boc-His(Bom)-OH, to obtain a protected peptide resin corresponding to Peptide 17; His(Bom)-Ser(Bzl)-Asp(OcHex)-Ala-Val-Phe-Thr(SEQ ID NO: 45) (Bzl)-Asp(OcHex)-Asn-Tyr(Cl$_2$-Bzl)-Thr(Bzl)-Arg (Tos)-Leu-Arg(Tos)-Arg(Tos)-Gln-Met-Ala-Val-Arg(SEQ ID NO: 49) (Tos)-Arg(Tos)-Tyr(Cl$_2$-Bzl)-Leu-Asn-Ser(Bzl)-Ile-MBHA.

To the resulting protected peptide-MBHA resin was added 100 mL of anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography (stepwise gradient between 10% acetonitrile and 50% acetonitrile), followed by lyophilizing to obtain Peptide 17.

Synthesis Example 5

Preparation of Peptide 18

Peptide 18 having an amino acid sequence shown in SEQ ID NO:18 was synthesized in the same manner as that of Peptide 5. Namely, coupling/deprotection was performed on a MBHA resin successively in an order of Boc-Ser(Bzl)-OH, Boc-Asn(Xan)-OH, Boc-Leu-OH, Boc-Tyr(Cl$_2$-Bzl)-OH, Boc-Arg(Tos)-OH, Boc-Arg(Tos)-OH, Boc-Val-OH, Boc-Ala-OH, Boc-Met-OH, Boc-Gln(Xan)-OH, Boc-Arg(Tos)-OH, Boc-Arg(Tos)-OH, Boc-Leu-OH, Boc-Arg (Tos)-OH, Boc-Thr(Bzl)-OH, Boc-Tyr (Cl$_2$-Bzl)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His(Bom)-OH, to obtain a protected peptide resin corresponding to Peptide 18; His(Bom)-Ser(Bzl)-Asp(OcHex)-Ala-Val-Phe-Thr(SEQ ID NO: 45) (Bzl)-Asp (OcHex)-Asn-Tyr (Cl$_2$-Bzl)-Thr (Bzl)-Arg (Tos)-Leu-Arg (Tos)-Arg(Tos)-Gln-Met-Ala-Val-Arg(SEQ ID NO: 49) (Tos)-Arg(Tos)-Tyr (Cl$_2$-Bzl)-Leu-Asn-Ser (Bzl)-MBHA.

To the resulting protected peptide-MBHA resin was added 100 mL of anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography (stepwise gradient between 10% acetonitrile and 50% acetonitrile), followed by lyophilizing to obtain Peptide 18.

Synthesis Example 6

Preparation of Peptide 19

Peptide 19 having an amino acid sequence shown in SEQ ID NO:19 was synthesized in the same manner as that of Peptide 5. Namely, coupling/deprotection was performed on a MBHA resin successively in an order of Boc-Asn(Xan)-OH, Boc-Leu-OH, Boc-Tyr (Cl$_2$-Bzl)-OH, Boc-Arg (Tos)-OH, Boc-Arg(Tos)-OH, Boc-Val-OH, Boc-Ala-OH, Boc-Met-OH, Boc-Gln(Xan)-OH, Boc-Arg(Tos)-OH, Boc-Arg (Tos)-OH, Boc-Leu-OH, Boc-Arg(Tos)-OH, Boc-Thr(Bzl)-OH, Boc-Tyr(Cl$_2$-Bzl)-OH, Boc-Asn(Xan)-OH, Boc-Asp (OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His(Bom)-OH, to obtain a protected peptide resin corresponding to Peptide 19; His(Bom)-Ser(Bzl)-Asp (OcHex)-Ala-Val-Phe-Thr(SEQ ID NO: 45) (Bzl)-Asp (OcHex)-Asn-Tyr(Cl$_2$-Bzl)-Thr(Bzl)-Arg(Tos)-Leu-Arg (Tos)-Arg(Tos)-Gln-Met-Ala-Val-Arg(SEQ ID NO: 49) (Tos)-Arg(Tos)-Tyr(Cl$_2$-Bzl)-Leu-Asn-MBHA.

To the resulting protected peptide-MBHA resin was added 100 mL of anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography (stepwise gradient between 10% acetonitrile and 50% acetonitrile), followed by lyophilizing to obtain Peptide 19.

Synthesis Example 7

Preparation of Peptide 20

Peptide 20 having an amino acid sequence shown in SEQ ID NO: 20 was synthesized in the same manner as that of Peptide 5. Namely, coupling/deprotection was performed on a MBHA resin successively in an order of Boc-Leu-OH, Boc-Tyr(Cl$_2$-Bzl)-OH, Boc-Arg(Tos)-OH, Boc-Arg(Tos)-OH, Boc-Val-OH, Boc-Ala-OH, Boc-Met-OH, Boc-Gln (Xan)-OH, Boc-Arg(Tos)-OH, Boc-Arg(Tos)-OH, Boc-Leu-OH, Boc-Arg(Tos)-OH, Boc-Thr(Bzl)-OH, Boc-Tyr(Cl$_2$-Bzl)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His (Bom)-OH, to obtain a protected peptide resin corresponding to Peptide 20; His(Bom)-Ser(Bzl)-Asp(OcHex)-Ala-Val-Phe-Thr(SEQ ID NO: 45) (Bzl)-Asp(OcHex)-Asn-Tyr(Cl$_2$-Bzl)-Thr(Bzl)-Arg(Tos)-Leu-Arg(Tos)-Arg(Tos)-Gln-Met-Ala-Val-Arg(SEQ ID NO: 49) (Tos)-Arg(Tos)-Tyr(Cl$_2$-Bzl)-Leu-MBHA.

To the resulting protected peptide-MBHA resin was added 100 mL of anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography (stepwise gradient between 10% acetonitrile and 50% acetonitrile), followed by lyophilizing to obtain Peptide 20.

Synthesis Example 8

Preparation of Peptide 21

Peptide 21 having an amino acid sequence shown in SEQ ID NO: 21 was synthesized in the same manner as that of Peptide 5. Namely, coupling/deprotection was performed on a MBHA resin successively in an order of Boc-Leu-OH, Boc-Ile-OH, Boc-Ser(Bzl)-OH, Boc-Asn(Xan)-OH, Boc-Leu-OH, Boc-Tyr($Cl_2$-Bzl)-OH, Boc-Arg(Tos)-OH, Boc-Arg(Tos)-OH, Boc-Val-OH, Boc-Ala-OH, Boc-Leu-OH, Boc-Gln(Xan)-OH, Boc-Arg(Tos)-OH, Boc-Arg(Tos)-OH, Boc-Leu-OH, Boc-Arg(Tos)-OH, Boc-Thr(Bzl)-OH, Boc-Tyr($Cl_2$-Bzl)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His(Bom)-OH, to obtain a protected peptide resin corresponding to Peptide 21; His(Bom)-Ser(Bzl)-Asp(OcHex)-Ala-Val-Phe-Thr(SEQ ID NO: 45) (Bzl)-Asp(OcHex)-Asn-Tyr($Cl_2$-Bzl)-Thr(Bzl)-Arg(Tos)-Leu-Arg(Tos)-Arg(Tos)-Gln-Leu-Ala-Val-Arg(SEQ ID NO: 46) (Tos)-Arg(Tos)-Tyr($Cl_2$-Bzl)-Leu-Asn-Ser(Bzl)-Ile-Leu-MBHA.

To the resulting protected peptide-MBHA resin was added 100 mL of anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography (stepwise gradient between 10% acetonitrile and 50% acetonitrile), followed by lyophilizing to obtain Peptide 21.

Synthesis Example 9

Preparation of Peptide 22

Peptide 22 having an amino acid sequence shown in SEQ ID NO: 22 was synthesized in the same manner as that of Peptide 5. Namely, coupling/deprotection was performed on a MBHA resin successively in an order of Boc-Ile-OH, Boc-Ser(Bzl)-OH, Boc-Asn(Xan)-OH, Boc-Leu-OH, Boc-Tyr($Cl_2$-Bzl)-OH, Boc-Arg(Tos)-OH, Boc-Arg(Tos)-OH, Boc-Val-OH, Boc-Ala-OH, Boc-Leu-OH, Boc-Gln(Xan)-OH, Boc-Arg(Tos)-OH, Boc-Arg(Tos)-OH, Boc-Leu-OH, Boc-Arg(Tos)-OH, Boc-Thr(Bzl)-OH, Boc-Tyr($Cl_2$-Bzl)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH and Boc-His(Bom)-OH, to obtain a protected peptide resin corresponding to Peptide 22; His(Bom)-Ser(Bzl)-Asp(OcHex)-Ala-Val-Phe-Thr(SEQ ID NO: 45) (Bzl)-Asp(OcHex)-Asn-Tyr($Cl_2$-Bzl)-Thr(Bzl)-Arg(Tos)-Leu-Arg(Tos)-Arg(Tos)-Gln-Leu-Ala-Val-Arg(SEQ ID NO: 46) (Tos)-Arg(Tos)-Tyr($Cl_2$-Bzl)-Leu-Asn-Ser(Bzl)-Ile-MBHA.

To the resulting protected peptide-MBHA resin was added 100 mL of anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography (stepwise gradient between 10% acetonitrile and 50% acetonitrile), followed by lyophilizing to obtain Peptide 22.

Synthesis Example 10

Preparation of Peptide 23

Peptide 23 having an amino acid sequence shown in SEQ ID NO: 23 was synthesized in the same manner as that of Peptide 5. Namely, coupling/deprotection was performed on a MBHA resin successively in an order of Boc-Ser(Bzl)-OH, Boc-Asn(Xan)-OH, Boc-Leu-OH, Boc-Tyr ($Cl_2$-Bzl)-OH, Boc-Arg(Tos)-OH, Boc-Arg(Tos)-OH, Boc-Val-OH, Boc-Ala-OH, Boc-Leu-OH, Boc-Gln(Xan)-OH, Boc-Arg(Tos)-OH, Boc-Arg(Tos)-OH, Boc-Leu-OH, Boc-Arg(Tos)-OH, Boc-Thr(Bzl)-OH, Boc-Tyr($Cl_2$-Bzl)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His(Bom)-OH, to obtain a protected resin corresponding to Peptide 23; His(Bom)-Ser(Bzl)-Asp(OcHex)-Ala-Val-Phe-Thr(SEQ ID NO: 45) (Bzl)-Asp(OcHex)-Asn-Tyr ($Cl_2$-Bzl)-Thr (Bzl)-Arg (Tos)-Leu-Arg (Tos)-Arg (Tos)-Gln-Leu-Ala-Val-Arg(SEQ ID NO: 46) (Tos)-Arg(Tos)-Tyr ($Cl_2$-Bzl)-Leu-Asn-Ser(Bzl)-MBHA.

To the resulting protected peptide-MBHA resin was added 100 mL of anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography (stepwise gradient between 10% acetonitrile and 50% acetonitrile), followed by lyophilizing to obtain Peptide 23.

Synthesis Example 11

Preparation of Peptide 24

Peptide 24 having an amino acid sequence shown in SEQ ID NO: 24 was synthesized in the same manner as that of Peptide 5. Namely, coupling/deprotection was performed on a MBHA resin successively in an order of Boc-Asn(Xan)-OH, Boc-Leu-OH, Boc-Tyr ($Cl_2$-Bzl)-OH, Boc-Arg(Tos)-OH, Boc-Arg(Tos)-OH, Boc-Val-OH, Boc-Ala-OH, Boc-Leu-OH, Boc-Gln (Xan)-OH, Boc-Arg (Tos)-OH, Boc-Arg (Tos)-OH, Boc-Leu-OH, Boc-Arg(Tos)-OH, Boc-Thr(Bzl)-OH, Boc-Tyr($Cl_2$-Bzl)-OH, Boc-Asn(Xan)-OH, Boc-Asp(OcHex)-OH, Boc-Thr(Bzl)-OH Boc-Phe-OH, Boc-Val-OH, Boc-Ala-OH, Boc-Asp(OcHex)-OH, Boc-Ser(Bzl)-OH, and Boc-His(Bom)-OH, to obtain a protected peptide resin corresponding to Peptide 24; His(Bom)-Ser(Bzl)-Asp(OcHex)-Ala-Val-Phe-Thr(SEQ ID NO: 45) (Bzl)-Asp(OcHex)-Asn-Tyr($Cl_2$-Bzl)-Thr(Bzl)-Arg(Tos)-Leu-Arg(Tos)-Arg(Tos)-Gln-Leu-Ala-Val-Arg(SEQ ID NO: 46) (Tos)-Arg(Tos)-Tyr($Cl_2$-Bzl)-Leu-Asn-MBHA.

To the resulting protected peptide-MBHA resin was added 100 mL of anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography (stepwise gradient between 10% acetonitrile and 50% acetonitrile), followed by lyophilizing to obtain Peptide 24.

Synthesis Example 12

Preparation of Peptide 25

Peptide 25 having an amino acid sequence shown in SEQ ID NO: 25 was synthesized in the same manner as that of Peptide 5. Namely, coupling/deprotection was performed on a MBHA resin successively in an order of Boc-Leu-OH, Boc-Tyr($Cl_2$-Bzl)-OH, Boc-Arg(Tos)-OH, Boc-Arg(Tos)-OH, Boc-Val-OH, Boc-Ala-OH, Boc-Leu-OH, Boc-Gln(Xan)-OH, Boc-Arg(Tos)-OH, Boc-Arg(Tos)-OH, Boc-Leu- OH, Boc-Arg(Tos)-OH, Boc-Thr (Bzl)-OH, Boc-Tyr(Cl₂-Bzl)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His(Bom)-OH, to obtain a protected peptide resin corresponding to Peptide 25; His(Bom)-Ser(Bzl)-Asp(OcHex)-Ala-Val-Phe-Thr(SEQ ID NO: 45) (Bzl)-Asp(OcHex)-Asn-Tyr(Cl₂-Bzl)-Thr(Bzl)-Arg(Tos)-Leu-Arg(Tos)-Arg(Tos)-Gln-Leu-Ala-Val-Arg (SEQ ID NO: 46) (Tos)-Arg (Tos)-Tyr (Cl₂-Bzl)-Leu-MBHA.

To the resulting protected peptide-MBHA resin was added 100 mL of anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography (stepwise gradient between 10% acetonitrile and 50% acetonitrile), followed by lyophilizing to obtain Peptide 25.

Synthesis Example 13

Preparation of Peptide 1

Peptide 1 having an amino acid sequence shown in SEQ ID NO: 1 was synthesized in the same manner as that of Peptide 5. Namely, coupling/deprotection was performed on a MBHA resin successively in an order of Boc-Gly-OH, Boc-Asn(Xan)-OH, Boc-Leu-OH, Boc-Ile-OH, Boc-Ser(Bzl)-OH, Boc-Asn(Xan)-OH, Boc-Leu-OH, Boc-Tyr(Cl₂-Z)-OH, Boc-Arg(Tos)-OH, Boc-Arg(Tos)-OH, Boc-Val-OH, Boc-Ala-OH, Boc-Leu-OH, Boc-Gln(Xan)-OH, Boc-Arg(Tos)-OH, Boc-Arg(Tos)-OH, Boc-Leu-OH, Boc-Arg(Tos)-OH, Boc-Thr(Bzl)-OH, Boc-Tyr(Cl₂-Z)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His(Bom)-OH, to obtain a protected peptide resin corresponding to Peptide 1; His(Bom)-Ser(Bzl)-Asp(OcHex)-Ala-Val-Phe-Thr(SEQ ID NO: 45) (Bzl)-Asp(OcHex)-Asn-Tyr(Cl₂-Bzl)-Thr(Bzl)-Arg(Tos)-Leu-Arg(Tos)-Arg(Tos)-Gln-Leu-Ala-Val-Arg (SEQ ID NO: 46) (Tos)-Arg (Tos)-Tyr (Cl₂-Bzl)-Leu-Asn-Ser(Bzl)-Ile-Leu-Asn-Gly-MBHA. To the resulting protected peptide-MBHA resin was added anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography, and lyophilized to obtain Peptide 1.

Synthesis Example 14

Preparation of Peptide 2

Peptide 2 having an amino acid sequence shown in SEQ ID NO: 2 was synthesized as in the process of preparing Peptide 5. Namely, coupling/deprotection was performed on a MBHA resin successively in an order of Boc-Lys(Cl-Z)-OH, Boc-Gly-OH, Boc-Asn(Xan)-OH, Boc-Leu-OH, Boc-Ile-OH, Boc-Ser(Bzl)-OH, Boc-Asn(Xan)-OH, Boc-Leu-OH, Boc-Tyr(Cl₂-Z)-OH, Boc-Arg(Tos)-OH, Boc-Arg(Tos)-OH, Boc-Val-OH, Boc-Ala-OH, Boc-Leu-OH, Boc-Gln(Xan)-OH, Boc-Arg(Tos)-OH, Boc-Arg(Tos)-OH, Boc-Leu-OH, Boc-Arg(Tos)-OH, Boc-Thr(Bzl)-OH, Boc-Tyr(Cl₂-Z)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His(Bom)-OH, to obtain a protected peptide resin corresponding to Peptide 2; His(Bom)-Ser(Bzl)-Asp(OcHex)-Ala-Val-Phe-Thr (SEQ ID NO: 45) (Bzl)-Asp(OcHex)-Asn-Tyr(Cl₂-Bzl)-Thr(Bzl)-Arg(Tos)-Leu-Arg(Tos)-Arg(Tos)-Gln-Leu-Ala-Val-Arg(SEQ ID NO: 46) (Tos)-Arg (Tos)-Tyr (Cl₂-Bzl)-Leu-Asn-Ser(Bzl)-Ile-Leu-Asn-Gly-Lys (SEQ ID NO: 50) (Cl-Z)-MBHA. To the resulting protected peptide-MBHA resin was added anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography, and lyophilized to obtain Peptide 2.

Synthesis Example 15

Preparation of Peptide 3

Peptide 3 having an amino acid sequence shown in SEQ ID NO: 3 was synthesized in the same manner as that of Peptide 5. Namely, coupling/deprotection was performed on a MBHA resin successively in an order of Boc-Arg(Tos)-OH, Boc-Gly-OH, Boc-Asn(Xan)-OH, Boc-Leu-OH, Boc-Ile-OH, Boc-Ser(Bzl)-OH, Boc-Asn(Xan)-OH, Boc-Leu-OH, Boc-Tyr(Cl₂-Z)-OH, Boc-Arg(Tos)-OH, Boc-Arg(Tos)-OH, Boc-Val-OH, Boc-Ala-OH, Boc-Leu-OH, Boc-Gln(Xan)-OH, Boc-Arg(Tos)-OH, Boc-Arg(Tos)-OH, Boc-Leu-OH, Boc-Arg(Tos)-OH, Boc-Thr(Bzl)-OH, Boc-Tyr(Cl₂-Z)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His(Bom)-OH, to obtain a protected peptide resin corresponding to Peptide 3; His(Bom)-Ser(Bzl)-Asp(OcHex)-Ala-Val-Phe-Thr(SEQ ID NO: 45) (Bzl)-Asp(OcHex)-Asn-Tyr(Cl₂-Bzl)-Thr(Bzl)-Arg(Tos)-Leu-Arg(Tos)-Arg(Tos)-Gln-Leu-Ala-Val-Arg(SEQ ID NO: 46) (Tos)-Arg(Tos)-Tyr(Cl₂-Bzl)-Leu-Asn-Ser(Bzl)-Ile-Leu-Asn-Gly-Arg (SEQ ID NO: 47) (Tos)-MBHA. To the resulting protected peptide-MBHA resin was added anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography, and lyophilized to obtain Peptide 3.

Synthesis Example 16

Preparation of Peptide 4

Peptide 4 having an amino acid sequence shown in SEQ ID NO: 4 was synthesized in the same manner as that of Peptide 5. Namely, coupling/deprotection was performed on a MBHA resin successively in an order of Boc-Arg(Tos)-OH, Boc-Lys(Cl-Z)-OH, Boc-Gly-OH, Boc-Asn(Xan)-OH, Boc-Leu-OH, Boc-Ile-OH, Boc-Ser(Bzl)-OH, Boc-Asn(Xan)-OH, Boc-Leu-OH, Boc-Tyr (Cl₂-Z)-OH, Boc-Arg(Tos)-OH, Boc-Arg(Tos)-OH, Boc-Val-OH, Boc-Ala-OH, Boc-Leu-OH, Boc-Gln(Xan)-OH, Boc-Arg(Tos)-OH, Boc-Arg(Tos)-OH, Boc-Leu-OH, Boc-Arg(Tos)-OH, Boc-Thr(Bzl)-OH, Boc-Tyr(Cl₂-Z)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His(Bom)-OH, to obtain a protected peptide resin corresponding to Peptide 4; His(Bom)-Ser(Bzl)-Asp(OcHex)-Ala-Val-Phe-Thr(SEQ ID NO: 45) (Bzl)-Asp(OcHex)-Asn-Tyr(Cl₂-Bzl)-Thr(Bzl)-Arg(Tos)-Leu-Arg (Tos)-Arg(Tos)-Gln-Leu-Ala-Val-Arg(SEQ ID NO: 46) (Tos)-Arg(Tos)-Tyr(Cl$_2$-Bzl)-Leu-Asn-Ser(Bzl)-Ile-Leu-Asn-Gly-Lys(SEQ ID NO: 50) (Cl-Z)-Arg(Tos)-MBHA. To the resulting protected peptide-MBHA resin was added anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography, and lyophilized to obtain Peptide 4.

Synthesis Example 17

Preparation of Peptide 6

Peptide 6 having an amino acid sequence shown in SEQ ID NO: 6 was synthesized in the same manner as that of Peptide 5. Namely, coupling/deprotection was performed on a PAM resin successively in an order of Boc-Arg(Tos)-OH, Boc-Lys (Cl-Z)-OH, Boc-Gly-OH, Boc-Asn(Xan)-OH, Boc-Leu-OH, Boc-Ile-OH, Boc-Ser(Bzl)-OH, Boc-Asn(Xan)-OH, Boc-Leu-OH, Boc-Tyr(Cl$_2$-Z)-OH, Boc-Arg(Tos)-OH, Boc-Arg (Tos)-OH, Boc-Val-OH, Boc-Ala-OH, Boc-Leu-OH, Boc-Gln(Xan)-OH, Boc-Arg(Tos)-OH, Boc-Arg(Tos)-OH, Boc-Leu-OH, Boc-Arg(Tos)-OH, Boc-Thr(Bzl)-OH, Boc-Tyr (Cl$_2$-Z)-OH, Boc-Asn Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His (Bom)-OH, to obtain a protected peptide resin corresponding to Peptide 6; His(Bom)-Ser(Bzl)-Asp(OcHex)-Ala-Val-Phe-Thr(SEQ ID NO: 45) (Bzl)-Asp(OcHex)-Asn-Tyr(Cl$_2$-Bzl)-Thr(Bzl)-Arg(Tos)-Leu-Arg(Tos)-Arg (Tos)-Gln-Leu-Ala-Val-Arg(SEQ ID NO: 46) (Tos)-Arg(Tos)-Tyr(Cl$_2$-Bzl)-Leu-Asn-Ser(Bzl)-Ile-Leu-Asn-Gly-Lys(SEQ ID NO: 50) (Cl-Z)-Arg(Tos)-PAM. To the resulting protected peptide-PAM resin was added anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography, and lyophilized to obtain Peptide 6.

Synthesis Example 18

Preparation of Peptide 7

Peptide 7 having an amino acid sequence shown in SEQ ID NO: 7 was synthesized in the same manner as that of Peptide 5. Namely, coupling/deprotection was performed on a PAM resin successively in an order of Boc-Asn(Xan)-OH, Boc-Leu-OH, Boc-Ile-OH, Boc-Ser(Bzl)-OH, Boc-Asn(Xan)-OH, Boc-Leu-OH, Boc-Tyr (Cl$_2$-Z)-OH, Boc-Lys(Cl-Z)-OH, Boc-Lys(Cl-Z)-OH, Boc-Val-OH, Boc-Ala-OH, Boc-Met-OH, Boc-Gln(Xan)-OH, Boc-Lys(Cl-Z)-OH, Boc-Arg (Tos)-OH, Boc-Leu-OH, Boc-Arg(Tos)-OH, Boc-Thr(Bzl)-OH, Boc-Tyr(Cl$_2$-Z)-OH, Boc-Asn(Xan)-OH, Boc-Asp (OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His(Bom)-OH, to obtain a protected peptide resin corresponding to Peptide 7; His(Bom)-Ser(Bzl)-Asp (OcHex)-Ala-Val-Phe-Thr(SEQ ID NO: 45) (Bzl)-Asp (OcHex)-Asn-Tyr(Cl$_2$-Bzl)-Thr(Bzl)-Arg(Tos)-Leu-Arg (Tos)-Arg(Tos)-Gln-Met-Ala-Val-Arg(SEQ ID NO: 49) (Tos)-Arg(Tos)-Tyr(Cl$_2$-Bzl)-Leu-Asn-Ser(Bzl)-Ile-Leu-Asn-PAM. To the resulting protected peptide-PAM resin was added anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography, and lyophilized to obtain Peptide 7.

Synthesis Example 19

Preparation of Peptide 8

Peptide 8 having an amino acid sequence shown in SEQ ID NO: 8 was synthesized in the same manner as that of Peptide 5. Namely, coupling/deprotection was performed on a MBHA resin successively in an order of Boc-Leu-OH, Boc-Ile-OH, Boc-Ser(Bzl)-OH, Boc-Asn(Xan)-OH, Boc-Leu-OH, Boc-Tyr(Cl$_2$-Z)-OH, Boc-Lys(Cl-Z)-OH, Boc-Lys(Cl-Z)-OH, Boc-Val-OH, Boc-Ala-OH, Boc-Met-OH, Boc-Gln (Xan)-OH, Boc-Lys(Cl-Z)-OH, Boc-Arg(Tos)-OH, Boc-Leu-OH, Boc-Arg(Tos)-OH, Boc-Thr(Bzl)-OH, Boc-Tyr (Cl$_2$-Z)-OH, Boc-Asn (Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His (Bom)-OH, to obtain a protected peptide resin corresponding to Peptide 8; His(Bom)-Ser(Bzl)-Asp(OcHex)-Ala-Val-Phe-Thr(SEQ ID NO: 45) (Bzl)-Asp(OcHex)-Asn-Tyr(Cl$_2$-Bzl)-Thr(Bzl)-Arg(Tos)-Leu-Arg(Tos)-Arg(Tos)-Gln-Met-Ala-Val-Arg(SEQ ID NO: 49) (Tos)-Arg(Tos)-Tyr(Cl$_2$-Bzl)-Leu-Asn-Ser(Bzl)-Ile-Leu-MBHA. To the resulting protected peptide-MBHA resin was added anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography, and lyophilized to obtain Peptide 8.

Synthesis Example 20

Preparation of Peptide 9

Peptide 9 having an amino acid sequence shown in SEQ ID NO: 9 was synthesized in the same manner as that of Peptide 5. Namely, coupling/deprotection was performed on a MBHA resin successively in an order of Boc-Ile-OH, Boc-Ser(Bzl)-OH, Boc-Asn(Xan)-OH, Boc-Leu-OH, Boc-Tyr (Cl$_2$-Z)-OH, Boc-Lys(Cl-Z)-OH, Boc-Lys(Cl-Z)-OH, Boc-Val-OH, Boc-Ala-OH, Boc-Met-OH, Boc-Gln(Xan)-OH, Boc-Lys(Cl-Z)-OH, Boc-Arg(Tos)-OH, Boc-Leu-OH, Boc-Arg(Tos)-OH, Boc-Thr(Bzl)-OH, Boc-Tyr(Cl$_2$-Z)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp (OcHex)-OH, Boc-Ser(Bzl)-OH and Boc-His(Bom)-OH, to obtain a protected peptide resin corresponding to Peptide 9; His(Bom)-Ser(Bzl)-Asp(OcHex)-Ala-Val-Phe-Thr(SEQ ID NO: 45) (Bzl)-Asp(OcHex)-Asn-Tyr(Cl$_2$-Bzl)-Thr(Bzl)-Arg (Tos)-Leu-Arg(Tos)-Arg(Tos)-Gln-Met-Ala-Val-Arg(SEQ ID NO: 49) (Tos)-Arg(Tos)-Tyr(Cl$_2$-Bzl)-Leu-Asn-Ser(Bzl)-Ile-MBHA. To the resulting protected peptide-MBHA resin was added anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography, and lyophilized to obtain Peptide 9.

Synthesis Example 21

Preparation of Peptide 10

Peptide 10 having an amino acid sequence shown in SEQ ID NO: 10 was synthesized in the same manner as that of Peptide 5. Namely, coupling/deprotection was performed on a MBHA resin successively in an order of Boc-Ser(Bzl)-OH, Boc-Asn(Xan)-OH, Boc-Leu-OH, Boc-Tyr(Cl$_2$-Z)-OH, Boc-Lys(Cl-Z)-OH, Boc-Lys(Cl-Z)-OH, Boc-Val-OH, Boc-Ala-OH, Boc-Met-OH, Boc-Gln(Xan)-OH, Boc-Lys(Cl-Z)-OH, Boc-Arg(Tos)-OH, Boc-Leu-OH, Boc-Arg(Tos)-OH, Boc-Thr(Bzl)-OH, Boc-Tyr(Cl$_2$-Z)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His(Bom)-OH, to obtain a protected peptide resin corresponding to Peptide 10; His(Bom)-Ser(Bzl)-Asp(OcHex)-Ala-Val-Phe-Thr(SEQ ID NO: 45) (Bzl)-Asp(OcHex)-Asn-Tyr (Cl$_2$-Bzl)-Thr (Bzl)-Arg (Tos)-Leu-Arg (Tos)-Arg(Tos)-Gln-Met-Ala-Val-Arg(SEQ ID NO: 49) (Tos)-Arg(Tos)-Tyr (Cl$_2$-Bzl)-Leu-Asn-Ser (Bzl)-MBHA. To the resulting protected peptide-MBHA resin was added anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography, and lyophilized to obtain Peptide 10.

Synthesis Example 22

Preparation of Peptide 11

Peptide 11 having an amino acid sequence shown in SEQ ID NO: 11 was synthesized in the same manner as that of Peptide 5. Namely, coupling/deprotection was performed on a MBHA resin successively in an order of Boc-Asn(Xan)-OH, Boc-Leu-OH, Boc-Tyr (Cl$_2$-Z)-OH, Boc-Lys(Cl-Z)-OH, Boc-Lys(Cl-Z)-OH, Boc-Val-OH, Boc-Ala-OH, Boc-Met-OH, Boc-Gln(Xan)-OH, Boc-Lys(Cl-Z)-OH, Boc-Arg(Tos)-OH, Boc-Leu-OH, Boc-Arg(Tos)-OH, Boc-Thr(Bzl)-OH, Boc-Tyr(Cl$_2$-Z)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His(Bom)-OH, to obtain a protected peptide resin corresponding to Peptide 11; His(Bom)-Ser(Bzl)-Asp(OcHex)-Ala-Val-Phe-Thr(SEQ ID NO: 45) (Bzl)-Asp(OcHex)-Asn-Tyr(Cl$_2$-Bzl)-Thr(Bzl)-Arg(Tos)-Leu-Arg(Tos)-Arg(Tos)-Gln-Met-Ala-Val-Arg(SEQ ID NO: 49) (Tos)-Arg(Tos)-Tyr(Cl$_2$-Bzl)-Leu-Asn-MBHA. To the resulting protected peptide-MBHA resin was added anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography, and lyophilized to obtain Peptide 11.

Synthesis Example 23

Preparation of Peptide 12

Peptide 12 having an amino acid sequence shown in SEQ ID NO: 12 was synthesized in the same manner as that of Peptide 5. Namely, coupling/deprotection was performed on a MBHA resin successively in an order of Boc-Leu-OH, Boc-Tyr(Cl$_2$-Z)-OH, Boc-Lys(Cl-Z)-OH, Boc-Lys(Cl-Z)-OH, Boc-Val-OH, Boc-Ala-OH, Boc-Met-OH, Boc-Gln(Xan)-OH, Boc-Lys(Cl-Z)-OH, Boc-Arg(Tos)-OH, Boc-Leu-OH, Boc-Arg(Tos)-OH, Boc-Thr(Bzl)-OH, Boc-Tyr(Cl$_2$-Z)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His(Bom)-OH, to obtain a protected peptide resin corresponding to Peptide 12; His(Bom)-Ser(Bzl)-Asp(OcHex)-Ala-Val-Phe-Thr(SEQ ID NO: 45) (Bzl)-Asp(OcHex)-Asn-Tyr(Cl$_2$-Bzl)-Thr(Bzl)-Arg(Tos)-Leu-Arg(Tos)-Arg(Tos)-Gln-Met-Ala-Val-Arg(SEQ ID NO: 49) (Tos)-Arg(Tos)-Tyr(Cl$_2$-Bzl)-Leu-MBHA. To the resulting protected peptide-MBHA resin was added anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography, and lyophilized to obtain Peptide 12.

Synthesis Example 24

Preparation of Peptide 13

Peptide 13 having an amino acid sequence shown in SEQ ID NO: 13 was synthesized in the same manner as that of Peptide 5. Namely, coupling/deprotection was performed on a MBHA resin successively in an order of Boc-Ser(Bzl)-OH, Boc-Asn(Xan)-OH, Boc-Leu-OH, Boc-Tyr(Cl$_2$-Z)-OH, Boc-Lys(Cl-Z)-OH, Boc-Lys(Cl-Z)-OH, Boc-Val-OH, Boc-Ala-OH, Boc-Leu-OH, Boc-Gln(Xan)-OH, Boc-Lys(Cl-Z)-OH, Boc-Arg(Tos)-OH, Boc-Leu-OH, Boc-Arg(Tos)-OH, Boc-Thr(Bzl)-OH, Boc-Tyr(Cl$_2$-Z)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His(Bom)-OH, to obtain a protected peptide resin corresponding to Peptide 13; His(Bom)-Ser(Bzl)-Asp(OcHex)-Ala-Val-Phe-Thr(SEQ ID NO: 45) (Bzl)-Asp(OcHex)-Asn-Tyr (Cl$_2$-Bzl)-Thr (Bzl)-Arg (Tos)-Leu-Arg (Tos)-Arg(Tos)-Gln-Leu-Ala-Val-Arg(SEQ ID NO: 46) (Tos)-Arg(Tos)-Tyr(Cl$_2$-Bzl)-Leu-Asn-Ser(Bzl)-MBHA. To the resulting protected peptide-MBHA resin was added anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography, and lyophilized to obtain Peptide 13.

Synthesis Example 25

Preparation of Peptide 14

Peptide 14 having an amino acid sequence shown in SEQ ID NO: 14 was synthesized in the same manner as that of Peptide 5. Namely, coupling/deprotection was performed on a MBHA resin successively in an order of Boc-Asn(Xan)-OH, Boc-Leu-OH, Boc-Tyr (Cl$_2$-Z)-OH, Boc-Lys(Cl-Z)-OH, Boc-Lys(Cl-Z)-OH, Boc-Val-OH, Boc-Ala-OH, Boc-Leu-OH, Boc-Gln(Xan)-OH, Boc-Lys(Cl-Z)-OH, Boc-Arg (Tos)-OH, Boc-Leu-OH, Boc-Arg (Tos)-OH, Boc-Thr (Bzl)-OH, Boc-Tyr (Cl$_2$-Z)-OH, Boc-Asn(Xan)-OH, Boc-Asp(OcHex)-OH, Boc-Thr(Bzl)-OH, Boc-Phe-OH, Boc-Val-OH, Boc-Ala-OH, Boc-Asp(OcHex)-OH, Boc-Ser(Bzl)-OH, and Boc-His(Bom)-OH, to obtain a protected peptide resin corresponding to Peptide 14; His(Bom)-Ser(Bzl)-Asp(OcHex)-Ala-Val-Phe-Thr(SEQ ID NO: 45) (Bzl)-Asp(OcHex)-Asn-Tyr(Cl$_2$-Bzl)-Thr(Bzl)-Arg(Tos)-Leu-Arg(Tos)-Arg(Tos)-Gln-Leu-Ala-Val-Arg(SEQ ID NO: 46) (Tos)-Arg(Tos)-Tyr(Cl$_2$-Bzl)-Leu-Asn-MBHA. To the resulting protected peptide-MBHA resin was added anhydrous hydrogen fluoride in the presence of anisole to react them. After the reaction, anhydrous hydrogen fluoride was distilled off under reduced pressure, the residue was washed with ether, and 10% acetic acid was added thereto to extract the peptide. The extract was purified by reverse phase column chromatography, and lyophilized to obtain Peptide 14.

Preparation Example 1

Eye Drops 1 to be Dissolved Upon Use

| | |
|---|---|
| Peptide 5 | 2 g |
| Sodium chloride | 0.9 g |
| Boric acid | 0.1 g |
| Borax | q.s. (pH 7.8) |
| Benzalkonium chloride | 0.005 g |
| Sodium edetate | 0.02 g |
| Purified water | ad. 100 mL |

In 100 mL of purified water, 5 g of Peptide 5 is dissolved and filtered through a membrane filter (0.45 μm). Each 2 mL portion of this solution is dispensed into a 5 mL-eye drop container, and lyophilized. In about 80 mL of purified water, 0.9 g of sodium chloride, 0.1 g of boric acid, 0.005 g of benzalkonium chloride and 0.02 g of sodium edetate are dissolved, and the pH is adjusted to 7.8 with borax, and then, a total volume is adjusted to 100 mL with purified water. This solution is filtered through a membrane filter (0.45 μm), and dispensed into a 5 mL ampoule and sealed to obtain a dissolving solution. Upon use, the dissolving solution is poured into the above 5 mL-eye drop container to obtain eye drops.

Preparation 2

Eye Drops 2 to be Dissolved Upon Use

| | |
|---|---|
| Peptide 15 | 0.1 g |
| Mannitol | 5 g |
| Boric acid | 0.1 g |
| Borax | q.s. (pH 7.8) |
| Benzalkonium chloride | 0.005 g |
| Sodium edetate | 0.02 g |
| Purified water | ad. 100 mL |

In 100 mL of purified water, 0.25 g of Peptide 15 and 12.5 g of mannitol are dissolved, and filtered through a membrane filter (0.45 μm). Each 2 mL portion of this solution is dispensed into a 5 mL-eye drop container, and lyophilized. In about 80 mL of purified water, 0.1 g of boric acid, 0.005 g of benzalkonium chloride and 0.02 g of sodium edetate are dissolved, and the pH is adjusted to 7.8 with borax, and a total volume is adjusted to 100 mL with purified water. This solution is filtered through a membrane filter (0.45 μm), and dispensed into a 5 mL ampoule and sealed to obtain a dissolving solution. Upon use, the dissolving solution is poured into the above 5 mL-eye drop container to obtain eye drops.

Preparation Example 3

One-Pack Type Eye Drops 1

| | |
|---|---|
| Peptide 5 | 0.1 g |
| Boric acid | 0.7 g |
| Borax | q.s. (pH 7.7) |
| Sodium chloride | 0.5 g |
| Sodium edetate | 0.05 g |
| Benzalkonium chloride | 0.005 g |
| Purified water | ad. 100 mL |

Sodium chloride, boric acid, sodium edetate and benzalkonium chloride are added to about 80 mL of purified water and dissolved therein, and the pH is adjusted to 7.7 by adding borax. Peptide 5 is added to this solution and dissolved therein, and then, a total volume is made up to 100 mL with purified water to obtain eye drops.

Preparation Example 4

One-Pack Type Eye Drops 2

| | |
|---|---|
| Peptide 15 | 0.5 g |
| Sodium chloride | 0.9 g |
| Sodium dihydrogen phosphate dihydrate | 0.1 g |
| Benzalkonium chloride | 0.005 g |
| 0.1 N sodium hydroxide | q.s. (pH 7.2) |
| Purified water | ad. 100 mL |

Sodium chloride, sodium dihydrogen phosphate·dihydrate and benzalkonium chloride are added to about 80 mL of purified water and dissolved therein, and the pH is adjusted to 7.2 by adding 0.1 N sodium hydroxide. Peptide 15 is added to this solution and dissolved therein, and then, a total volume is made up to 100 mL with purified to obtain eye drops.

Preparation Example 5

Injectable Preparation 1

In water for injection, 1.0 mg of Peptide 5, 200 mg of sodium chloride and 300 mg of gelatin are dissolved. An appropriate amount of a pH adjusting agent is added thereto so as to adjust pH to 7.4, a total volume is made up to 20 mL with water for injection, and the solution is sterilized by filtration, each 2 mL portion of which is dispensed into a glass ampoule.

Preparation Example 6

Injectable Preparation 2

In water for injection, 1.0 mg of Peptide 15, 200 mg of sodium chloride and 250 mg of albumin are dissolved. An appropriate amount of a pH adjusting agent is added thereto so as to adjust pH to 7.4, a total volume is made up to 20 mL with water for injection, and the solution is sterilized by filtration, each 2 mL portion of which is dispensed into a glass ampoule.

Test Example 1

Trypsin Digestion Test

The effect of highly basified Peptide 5 on digestion with trypsin was studied in the presence of chondroitin sulfate.
1) Test Method
To 100 μL of a solution of VIP and Peptide 5 (1 mg/mL) was added 400 μL of a solution of chondroitin sulfate (pH 7.5, 100 μg/mL) in a 0.2 M Tris-HCl buffer (pH 7.5). To 100 μL of this solution was added 0.5 mU of trypsin and the mixture was incubated at 37° C. for 180 minutes. Then, an amount of an undegraded peptide was measured by HPLC.

2) Results

In digestion by trypsin in the presence of chondriotin sulfate, the remaining rate of VIP was 75%, while that of Peptide 5 was as high as 89%. This result suggests that interaction of this peptide and acidic polysaccharides exhibits resistance to enzymatic degradation.

Test Example 2

Digestion Test with Bronchoalveolar Lavage Fluid

The effect of highly basified Peptide 5 on digestion with bronchoalveolar lavage fluid was studied.

1) Test Method

VIP and Peptide 5 were dissolved (1.1 mg/mL) in a 0.2% Tris-HCl buffer (pH 7.4), and bronchoalveolar lavage fluid (BALF) was added thereto. BALF was obtained by pouring 5 mL of a physiological saline into a trachea of a 8 to 9 week old normal SD male rat (about 350 g) under anesthesia, and recovering the saline, and repeating this procedure totally three times. To 0.5 mL of BALF was added 0.05 mL of a sample solution and the mixture was reacted at 37° C. for 90 minutes, and thereafter an amount of undegraded peptide was measured by HPLC.

2) Results

In a digestion test with BALF, the remaining rate of VIP was 45.5%, while the remaining rate of Peptide 5 was 80.0%, demonstrating about 1.8-fold higher remaining rate as compared with VIP. This result suggests that this peptide exhibits the excellent stability in a living body.

Test Example 3

Activity of Promoting Secretion of Protein from Isolated Lacrimal Grand

An isolated lacimal gland of a rabbit was treated with VIP, or Peptide 5 or 15, and the pharmacological effect of these peptides on increase in an amount of secreted protein was studied.

1) Preparation of Test Solution a) Purified water was added to sodium chloride (137.92 g), potassium chloride (7.01 g), calcium chloride-dihydrate (3.53 g) and magnesium chloride.hexahydrate (1.2 g) and the mixture was made up to a total volume of 1000 mL (Solution 1). Separately, purified water was added to potassium dihydrogen phosphate (8.17 g) and the mixture was made up to a total volume of 500 mL (Solution 2). Solution 1 (50 mL) and Solution 2 (10 mL) were added to 900 mL of purified water, 2.07 g of glucose and 2.1 g of sodium dicarbonate were dissolved therein, a total amount was adjusted to 1000 mL (pH about 7.4) to obtain an incubation medium. The incubation medium was bubbled with mixed gas containing 95% oxygen and 5% carbon dioxide.

b) VIP, Peptide 5 or Peptide 15 was dissolved in the incubation medium at a concentration of $10^{-4}$ M to obtain a test solution.

2) Preparation of Lacrimal Gland Piece Specimen

A male Japanese white rabbit was systemically anesthetized, a perfusion solution (containing 116 mM sodium chloride, 5.4 mM potassium chloride) was perfused through an abdominal aorta, a main lacrimal gland tissue was isolated, and a fat connective tissue was removed, which was divided equally (one piece was about 40 mg). This lacrimal gland tissue piece was transferred to a 24-well plate wherein each well thereof was filled with 0.5 mL of the incubation medium, followed by incubation at 37° C. The incubation medium was exchanged every 20 minutes three times, allowed to stand for a total of 60 minutes, to obtain a lacrimal gland piece specimen in the steady state.

3) Test Method a) The piece specimen in the steady state was used, the incubation medium was exchanged with 0.5 mL of a fresh incubation medium, followed by incubation at 37° C. for 20 minutes. This incubation medium was collected, a protein staining reagent (DC Protein assay reagent, Bio Rad) was added thereto, and an amount of protein was measured and expressed as an amount of secreted protein per mg of wet weight. An amount of protein thereupon was regarded as protein secretion rate 100%, and used as a secretion rate before treatment.

b) The incubation medium of the piece specimen after incubation in a) was exchanged with 0.5 mL of a test solution, and the solution was exchanged and collected at 20 minutes intervals totally five times. A protein staining reagent was added to the collected solution, and an amount of protein was measured. For a piece specimen in a control group, the incubation medium was exchanged similarly, and an amount of protein was measured.

4) Results

The test results are shown in FIG. 1. A vertical axis indicates a rate (%) of protein secretion from isolated lacrimal gland, and a horizontal axis indicates a time (min.) of treatment with each test solution. When treated with VIP, Peptide 5 and Peptide 15, a rate of protein secretion was significantly increased for a treating time of 0 to 40 minutes as compared with a control group (n=5, mean±standard error, *; $p<0.05$, **; $p<0.01$, Dunnett's test). Namely, it has been revealed that all of Peptides 5 and 15 and VIP have the excellent protein secretion promoting activity.

Test Example 4

Lacrimal Secretion Promotion Activity of Eye Drops (1)

Peptide 5 or 15 was applied to eyes of a rabbit, and an amount of secreted tears was measured, whereby, the pharmacological effect of these peptides on increase in an amount of lacrimal secretion was studied.

1) Preparation of Solution

Purified water was added to sodium chloride (0.9 g) and sodium dihydrogen phosphate.dihydrate (0.1 g) to make up to a total volume of 100 mL. Further, an appropriate amount of aqueous sodium hydroxide solution was added so as to adjust pH to 7.0 to obtain a vehicle. Peptide 5 was dissolved in the vehicle at a concentration of 0.1 w/v %, and Peptide 15 was dissolved in the vehicle at a concentration of 2.0 w/v %, to prepare test solutions.

2) Test Method

Measurement of an amount of tears was performed by a Schirmer test. To eyes of a Japanese white rabbit, 50 μL of a test solution was applied once, and amounts of lacrimal secretion before and 10 minutes after the application to eyes were measured. Five minutes before measurement of an amount of tears, 10 μL of 0.4 w/v % oxybuprocaine hydrochloride (Anelocal™ eye drops, Senju Pharmaceutical Co., Ltd.) was dropped to topically anesthetize. After tears in palpebra interior conjunctival sac were wiped out using a filter paper, and an amount of lacrimal secretion for 1 minute was measured using a Schirmer test paper (Showa Yakuhin Kako Co., Ltd.).

3) Results

The test results are shown in Table 2. By single application to eyes of a rabbit, an amount of lacrimal secretion was significantly increased in application of the Peptide 5 solution (*; p<0.01, paired t test). In addition, in application of the Peptide 15 solution, a statistically significant difference was not recognized, but a tendency of increase was shown (p=0.13, paired t test).

Namely, it has been revealed that Peptides 5 and 15 have excellent lacrimal secretion promotion activity.

TABLE 2

| Amount of lacrimal secretion (Schirmer's value: mm/min, n = 6, mean ± standard error) | | |
|---|---|---|
| | Before administration | After administration |
| 0.1% Peptide 5 | 2.00 ± 0.62 | 8.92 ± 0.45* |
| 2.0% Peptide 15 | 3.25 ± 1.20 | 7.75 ± 2.16 |

Test Example 5

Lacrimal Secretion Promotion Activity of Eye Drops (2)

In the same manner as that of Test Example 4, Peptide 5 was applied, and an amount of lacrimal secretion was measured. In this test, an amount of lacrimal secretion was measured with time, and the effect was compared with that of VIP.

1) Preparation of Solution

Preparation of a solution was performed in the same manner as that of Test Example 4, and VIP and Peptide 5 were dissolved in the vehicle at a concentration of 0.1 w/v %, to prepare a test solution.

2) Test Method

50 μL of the vehicle or a test solution was applied to eyes of a Japanese white rabbit once, and amounts of lacrimal secretion were measured before and 10 minutes, 20 minutes, 30 minutes, 60 minutes and 100 minutes after the application. Measurement of an amount of lacrimal secretion was performed in the same manner as that of Test Example 4.

3) Results

Figure 2:
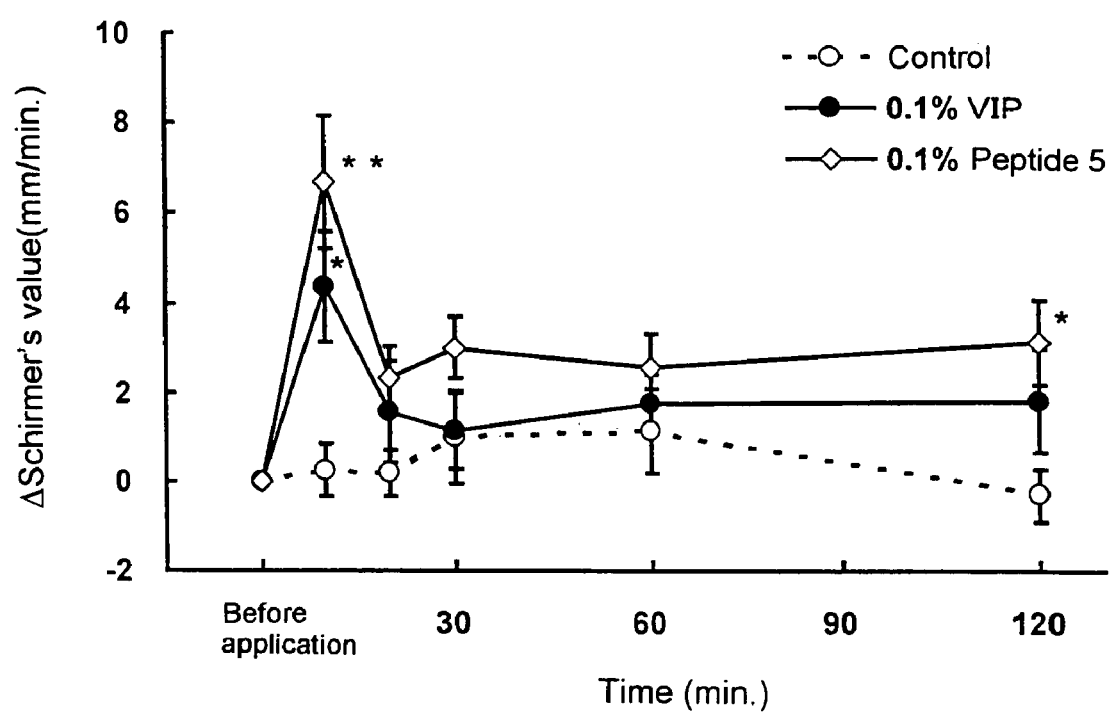
FIG. 2 shows an increment of lacrimal secretion amounts (Schirmer's value) with time, when VIP or Peptide 5 is applied to the eyes of a rabbit once.

A change in an amount of lacrimal secretion after administration is shown in FIG. 2. A vertical axis indicates a difference (increment) in an amount of lacrimal liquid secretion (Schirmer's value: mm/min.) from that before administration. A horizontal axis indicates passage of time (min.). By application of VIP and Peptide 5 to eyes, the amount was significantly increased at 10 minutes after the administration as compared with a control group of base administration (n=8, mean±standard error, *; p<0.05, **; p<0.01, parametric Dunnett-type multiple comparison test). An accumulated value of an increment of an amount of lacrimal secretion for 120 minutes after the administration (AUC value=ΔSchirmer's value×min.) is shown in Table 3. The AUC value is in an order of Peptide 5 administered group>VIP administered group>control group, and a Peptide 5 applied group shows a significantly higher value as compared with a control group (*; p<0.05). On the other hand, in a VIP applied group, a significant difference is not recognized as compared with a control group (p=0.38). Namely, it has been revealed that Peptide 5 has the excellent lacrimal secretion promoting activity as compared with VIP.

TABLE 3

| Accumulated value of increment of amount of lacrimal secretion after application | |
|---|---|
| Administered group | $AUC_{0-120\ min}$ (ΔSchirmer's value × min.) |
| Vehicle administered group (control group) | 65.6 ± 72.9 |
| 0.1% VIP administered group | 215.0 ± 98.2 |
| 0.1% Peptide 5 administered group | 359.2 ± 85.0* | n = 8, average ± standard error
*p < 0.05, parametric Dunnett-type multiple comparison test

INDUSTRIAL APPLICABILITY

The above results demonstrate that the VIP derivative of the present invention has the excellent lacrimal secretion promoting activity, and is useful as a remedy for dry eye and diseases associated with dry eye.

The invention claimed is:

1. A method for treating dry eye or dry eye associated with disease, comprising topically administering to an eye of a warm-blooded animal in need thereof an eye drop comprising 0.01-0.5% w/v % of a peptide selected from the group consisting of:

His-Ser-Asp-Ala-Val-Phe-Thr-Asp-Asn-Tyr-Thr-Arg-Leu-Arg-Arg-Gln-Leu-Ala-Val-Arg-Arg-Tyr-Leu-Asn-Ser-Ile-Leu-Asn-Gly (SEQ ID NO:1),

His-Ser-Asp-Ala-Val-Phe-Thr-Asp-Asn-Tyr-Thr-Arg-Leu-Arg-Arg-Gln-Leu-Ala-Val-Arg-Arg-Tyr-Leu-Asn-Ser-Ile-Leu-Asn-Gly-Lys (SEQ ID NO:2),

His-Ser-Asp-Ala-Val-Phe-Thr-Asp-Asn-Tyr-Thr-Arg-Leu-Arg-Arg-Gln-Leu-Ala-Val-Arg-Arg-Tyr-Leu-Asn-Ser-Ile-Leu-Asn-Gly-Arg (SEQ ID NO:3),

His-Ser-Asp-Ala-Val-Phe-Thr-Asp-Asn-Tyr-Thr-Arg-Leu-Arg-Arg-Gln-Leu-Ala-Val-Arg-Arg-Tyr-Leu-Asn-Ser-Ile-Leu-Asn-Gly-Lys-Arg (SEQ ID NO:4),

His-Ser-Asp-Ala-Val-Phe-Thr-Asp-Asn-Tyr-Thr-Arg-Leu-Arg-Arg-Gln-Leu-Ala-Val-Arg-Arg-Tyr-Leu-Asn-Ser-Ile-Leu-Asn-Gly-Arg-Arg (SEQ ID NO:5), and His-Ser-Asp-Ala-Val-Phe-Thr-Asp-Asn-Tyr-Thr-Arg-Leu-Arg-Arg-Gln-Leu-Ala-Val-Arg-Arg-Tyr-Leu-Asn-Ser-Ile-Leu-Asn-Gly-Lys-Arg (SEQ ID NO:6) wherein the C-terminus is optionally amidated with NH2, or a pharmaceutically acceptable salt thereof.

2. The method of claim 1, wherein the peptide is SEQ ID NO:5 and the C-terminus is amidated.

* * * * *

SEQUENCE LISTING

<160> NUMBER OF SEQ ID NOS: 25

<210> SEQ ID NO 1
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 1

His Ser Asp Ala Val Phe Thr Asp Asn Tyr Thr Arg Leu Arg Arg Gln
                 5                  10                  15

Leu Ala Val Arg Arg Tyr Leu Asn Ser Ile Leu Asn Gly
             20                  25

<210> SEQ ID NO 2
<211> LENGTH: 30
<212> TYPE: PRT
<213> ORGANISM: Artificial Sequence

```
<220> FEATURE:
<223> OTHER INFORMATION: Synthetic Peptide

<400> SEQUENCE: 2

His Ser Asp Ala Val Phe Thr Asp Asn Tyr Thr Arg Leu Arg Arg Gln
                 5                  10                  15

Leu Ala Val Arg Arg Tyr Leu Asn Ser Ile Leu Asn Gly Lys
             20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 3

His Ser Asp Ala Val Phe Thr Asp Asn Tyr Thr Arg Leu Arg Arg Gln
                 5                  10                  15

Leu Ala Val Arg Arg Tyr Leu Asn Ser Ile Leu Asn Gly Arg
             20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 4

His Ser Asp Ala Val Phe Thr Asp Asn Tyr Thr Arg Leu Arg Arg Gln
                 5                  10                  15

Leu Ala Val Arg Arg Tyr Leu Asn Ser Ile Leu Asn Gly Lys Arg
             20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 5

His Ser Asp Ala Val Phe Thr Asp Asn Tyr Thr Arg Leu Arg Arg Gln
                 5                  10                  15

Leu Ala Val Arg Arg Tyr Leu Asn Ser Ile Leu Asn Gly Arg Arg
             20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 6

His Ser Asp Ala Val Phe Thr Asp Asn Tyr Thr Arg Leu Arg Arg Gln
                 5                  10                  15

Leu Ala Val Arg Arg Tyr Leu Asn Ser Ile Leu Asn Gly Lys Arg
             20                  25                  30
```

<210> SEQ ID NO 7
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 7

His Ser Asp Ala Val Phe Thr Asp Asn Tyr Thr Arg Leu Arg Lys Gln
              5                   10                  15

Met Ala Val Lys Lys Tyr Leu Asn Ser Ile Leu Asn
            20                  25

<210> SEQ ID NO 8
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 8

His Ser Asp Ala Val Phe Thr Asp Asn Tyr Thr Arg Leu Arg Lys Gln
              5                   10                  15

Met Ala Val Lys Lys Tyr Leu Asn Ser Ile Leu
            20                  25

<210> SEQ ID NO 9
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 9

His Ser Asp Ala Val Phe Thr Asp Asn Tyr Thr Arg Leu Arg Lys Gln
              5                   10                  15

Met Ala Val Lys Lys Tyr Leu Asn Ser Ile
            20                  25

<210> SEQ ID NO 10
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 10

His Ser Asp Ala Val Phe Thr Asp Asn Tyr Thr Arg Leu Arg Lys Gln
              5                   10                  15

Met Ala Val Lys Lys Tyr Leu Asn Ser
            20                  25

<210> SEQ ID NO 11
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 11

His Ser Asp Ala Val Phe Thr Asp Asn Tyr Thr Arg Leu Arg Lys Gln
              5                   10                  15

Met Ala Val Lys Lys Tyr Leu Asn
            20

```
<210> SEQ ID NO 12
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 12

His Ser Asp Ala Val Phe Thr Asp Asn Tyr Thr Arg Leu Arg Lys Gln
                 5                  10                  15

Met Ala Val Lys Lys Tyr Leu
            20

<210> SEQ ID NO 13
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 13

His Ser Asp Ala Val Phe Thr Asp Asn Tyr Thr Arg Leu Arg Lys Gln
                 5                  10                  15

Leu Ala Val Lys Lys Tyr Leu Asn Ser
            20                  25

<210> SEQ ID NO 14
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 14

His Ser Asp Ala Val Phe Thr Asp Asn Tyr Thr Arg Leu Arg Lys Gln
                 5                  10                  15

Leu Ala Val Lys Lys Tyr Leu Asn
            20

<210> SEQ ID NO 15
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 15

His Ser Asp Ala Val Phe Thr Asp Asn Tyr Thr Arg Leu Arg Lys Gln
                 5                  10                  15

Leu Ala Val Lys Lys Tyr Leu
            20

<210> SEQ ID NO 16
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 16

His Ser Asp Ala Val Phe Thr Asp Asn Tyr Thr Arg Leu Arg Arg Gln
                 5                  10                  15

Met Ala Val Arg Arg Tyr Leu Asn Ser Ile Leu
            20                  25
```

```
<210> SEQ ID NO 17
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 17

His Ser Asp Ala Val Phe Thr Asp Asn Tyr Thr Arg Leu Arg Arg Gln
                 5                  10                  15

Met Ala Val Arg Arg Tyr Leu Asn Ser Ile
             20                  25

<210> SEQ ID NO 18
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 18

His Ser Asp Ala Val Phe Thr Asp Asn Tyr Thr Arg Leu Arg Arg Gln
                 5                  10                  15

Met Ala Val Arg Arg Tyr Leu Asn Ser
             20                  25

<210> SEQ ID NO 19
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 19

His Ser Asp Ala Val Phe Thr Asp Asn Tyr Thr Arg Leu Arg Arg Gln
                 5                  10                  15

Met Ala Val Arg Arg Tyr Leu Asn
             20

<210> SEQ ID NO 20
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 20

His Ser Asp Ala Val Phe Thr Asp Asn Tyr Thr Arg Leu Arg Arg Gln
                 5                  10                  15

Met Ala Val Arg Arg Tyr Leu
             20

<210> SEQ ID NO 21
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 21

His Ser Asp Ala Val Phe Thr Asp Asn Tyr Thr Arg Leu Arg Arg Gln
                 5                  10                  15

Leu Ala Val Arg Arg Tyr Leu Asn Ser Ile Leu
             20                  25
```

```
<210> SEQ ID NO 22
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 22

His Ser Asp Ala Val Phe Thr Asp Asn Tyr Thr Arg Leu Arg Arg Gln
                 5                  10                  15

Leu Ala Val Arg Arg Tyr Leu Asn Ser Ile
             20                  25

<210> SEQ ID NO 23
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 23

His Ser Asp Ala Val Phe Thr Asp Asn Tyr Thr Arg Leu Arg Arg Gln
                 5                  10                  15

Leu Ala Val Arg Arg Tyr Leu Asn Ser
             20                  25

<210> SEQ ID NO 24
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 24

His Ser Asp Ala Val Phe Thr Asp Asn Tyr Thr Arg Leu Arg Arg Gln
                 5                  10                  15

Leu Ala Val Arg Arg Tyr Leu Asn
             20

<210> SEQ ID NO 25
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 25

His Ser Asp Ala Val Phe Thr Asp Asn Tyr Thr Arg Leu Arg Arg Gln
                 5                  10                  15

Leu Ala Val Arg Arg Tyr Leu
             20
```